United States Patent [19]

Breeser et al.

[11] Patent Number: 5,601,783
[45] Date of Patent: Feb. 11, 1997

[54] VESSEL TRANSPORT DEVICE FOR AUTOMATIC CHEMICAL ANALYSIS

[75] Inventors: David Breeser, St. Paul; Alan Wirbisky, Eden Prairie; Ross Krogh, Waconia, all of Minn.

[73] Assignee: Pasteur Sanofi Diagnostics, France

[21] Appl. No.: 260,183

[22] Filed: Jun. 15, 1994

Related U.S. Application Data

[63] Continuation-in-part of Ser. No. 175,424, filed as PCT/US93/04209, Apr. 5, 1993, abandoned.

[51] Int. Cl.$^6$ ..................................................... G01N 35/04
[52] U.S. Cl. ............................... 422/65; 422/63; 436/43; 436/47; 436/48; 198/773
[58] Field of Search ................................. 436/45, 47, 43, 436/44; 422/65, 63, 66, 104; 198/773, 468.01, 468.9, 468.2

[56] References Cited

U.S. PATENT DOCUMENTS

| | | | |
|---|---|---|---|
| 3,578,412 | 5/1971 | Martin | 422/65 |
| 3,775,909 | 12/1973 | Best et al. | |
| 4,634,575 | 1/1987 | Kawakami | 422/63 |
| 4,689,202 | 8/1987 | Khoja | 422/65 |
| 4,693,867 | 9/1987 | Commarmot | |
| 4,835,707 | 5/1989 | Amano | 364/497 |
| 4,857,471 | 8/1989 | Salzman | |
| 5,055,261 | 10/1991 | Khoja | |
| 5,316,726 | 5/1994 | Babson et al. | 422/65 |
| 5,350,564 | 9/1994 | Mazza | 422/63 |

FOREIGN PATENT DOCUMENTS

| | | |
|---|---|---|
| 2519111 | 7/1976 | Germany |
| 2855088 | 7/1980 | Germany |
| 9322686 | 11/1993 | WIPO |

OTHER PUBLICATIONS

Ingenious Mechanisms for designers and inventors, Jones, vol. I, pp. 1–27; vol. II, pp. 1–61 and pp. 444–447; vol. III, pp. 1–19.

*Primary Examiner*—Long V. Le
*Attorney, Agent, or Firm*—Fredrikson & Byron, PA

[57] ABSTRACT

The present invention provides a vessel shuttle which can be used, for example, for moving reaction vessels to or from an assay resource station in an automated chemical analyzer. The vessel shuttle has a plurality of movable plates including first and second vessel carrying plates adapted to move cooperatively with respect to one another to advance a vessel stepwise along a linear path without net motion of the first and second vessel carrying plates as the vessel is advanced one step. In a preferred embodiment, the first and second vessel carrying plates each comprise a plurality of fingers defining recesses for receiving vessels and the first vessel carrying plate is adapted to move in a direction substantially perpendicular to the vessels' linear path and the second vessel carrying plate is adapted to move rectilinearly both generally parallel to and generally perpendicular to that linear path. The present invention may also include a waste chute for disposing of spent reaction vessels, the waste chute having a novel gate design. In accordance with this embodiment, the vessel shuttle can move a new vessel to a position for access by a pipettor or the like, transport a reaction vessel from the vessel shuttle to an adjacent assay resource station, and transport a reaction vessel from that assay resource station to the waste chute in one motion of the vessel shuttle.

8 Claims, 14 Drawing Sheets

Fig. 15

VESSEL TRANSPORT DEVICE FOR AUTOMATIC CHEMICAL ANALYSIS

This application is a continuation-in-part of U.S. patent application No. 08/175,424, now abandoned, which was filed Dec. 23, 1993 as a national stage patent application of International Patent Application PCT/US93/04209, itself filed May 4, 1993, and claiming priority from U.S. patent application No. 07/878,956, filed May 5, 1992, now U.S. Pat. No. 5,380,487.

FIELD OF THE INVENTION

The present invention relates to mechanisms for conveying items along a predefined path. In particular, the present invention provides an apparatus which has particular utility in moving sample vessels and the like for use in devices such as automated chemical analyzers.

BACKGROUND OF THE INVENTION

Automated chemical analyzers have proven to be useful tools in clinical laboratory settings. Quantitative chemical analysis requires precise control of such factors as time of reaction, temperature and reagent concentration. Tests manually conducted typically lack precise control of these parameters resulting in inaccurate or irreproducible results. Additionally, manual testing limits the speed of processing, makes the handling of large numbers of samples difficult and introduces the possibility of human error, such as misidentification of samples.

Fully automated chemical analyzers automatically obtain a volume of a patient sample suspected of containing a particular analyte, add reagents to the sample and control reaction parameters such as time and temperature. Such analyzers usually include a transport or conveyor system designed to transport containers of reaction mixtures of sample and reagents to various operating stations. Reactions between analyte in the sample and reagents result in a detectable signal automatically measurable by the instrument. A number of automated chemical analyzers are currently available on the market. Volume 14 of the *Journal of Clinical Immunoassay*, Summer 1991, ("J. Clin. Immun."), the teachings of which are incorporated herein by reference, provides a description of several of such automated analyzers.

The transport mechanisms used in automated analyzers and similar equipment typically have several design constraints. For example, the size of the analyzer is optimally kept relatively small to minimize the space required by the analyzer in the laboratory. Hence, space is frequently at a premium and there is a significant incentive to keep the transport mechanisms used in such analyzers as compact as reasonably possible.

Additionally, if the vessels moved by these transport mechanisms are moved jerkily along a path, the contents of the vessels can splash either upwards along the vessel walls, or even out of the vessel. The accuracy of many automated analyzers can be adversely affected by such splashing either because a critical quantity of the solution is lost from the vessel or clings to the vessel walls and does not fully react with the other reagents in the vessel. Accordingly, transport mechanisms used in chemical analyzers and the like should advance the vessels along a chosen path relatively smoothly to avoid such splashing.

A variety of different vessel transport systems have been proposed for transporting reaction vessels through a chemical analyzer or the like. In most such systems, the vessels are held in rigid rings or by flexible belts. The rigid rings may comprise a ring having a planar support and a ring having a series of flanges which are rigidly attached to a rotating ring. By turning the ring, the fingers engage the vessels and move them along the support. The time a vessel spends on such a rigid ring is usually critical to some operation of the analyzer, such as incubating the vessels for a set period of time. In order to ensure a sufficient dwell time, the area occupied by such rigid rings in an analyzer tends to be relatively large.

Belt-based systems can also use a rigid support, but will use a flexible belt having flanges for engaging the vessels rather than a rigid ring. Although systems using belts could conceivably be made more compact than rigid rings due to the flexibility of the belts, most belt-based systems do not seem to have taken advantage of this flexibility to yield a more compact structure. In addition, the flexibility of the belts and the manner in which such belts tend to be driven within an analyzer tend to increase the possibility of splashing of the vessel contents if steps are not taken to ensure relatively smooth acceleration and deceleration of the belt as it moves along its path.

Accordingly, there is a need in the art to provide a stable, reliable system for transporting vessels in chemical analyzers and the like which will be compact and will minimize splashing of the contents of the vessels. As detailed below, a vessel transport system of the present invention provides a compact, reliable mechanism for transporting reaction vessels along a predefined path.

SUMMARY OF THE INVENTION

The present invention provides a conveying mechanism which can be used as a vessel shuttle in a chemical analyzer to move vessels from one location in such an analyzer to another. For example, the vessel shuttle may be positioned in a chemical analyzer or the like so that assay constituents may be delivered to a reaction vessel while the vessel is on the shuttle. The vessel can then be transferred to another assay resource (e.g. an incubation station or a wash station), eliminating any need to delay transport of other reaction vessels through the other assay resources during the delivery of the assay constituents.

The vessel shuttle of the invention may include first and second movable vessel carrying plates, each plate having a plurality of fingers defining recesses for receiving vessels, the plates being adapted to move cooperatively with respect to one another to transport vessels stepwise along a linear path. A vessel transport of this type provides a novel and unique method and apparatus for moving vessels within an automated analyzer.

In automated chemical analyzers, vessels are typically transported using a chain or on a moving floor along a closed path and wherein the vessel carrying mechanism moves along the path with the vessel. The preferred vessel shuttle of this invention allows vessels to move through an analyzer stepwise along an open-ended path. The vessel shuttle of the invention includes first and second vessel carrying plates adapted to move cooperatively with respect to one another to move vessels along the path with no net motion of the vessel carrying plates, conserving space within the analyzer. Furthermore, since the vessels are moved along a straight path along a relatively smooth floor, splashing of the vessels' contents is minimized.

BRIEF DESCRIPTION OF THE DRAWINGS

FIGS. 12–15 are top isolation views of a portion of the vessel transport of FIG. 10 schematically illustrating operation of the lower vessel carrying plate of the transport.

DETAILED DESCRIPTION OF THE PREFERRED EMBODIMENTS

Figure 1:
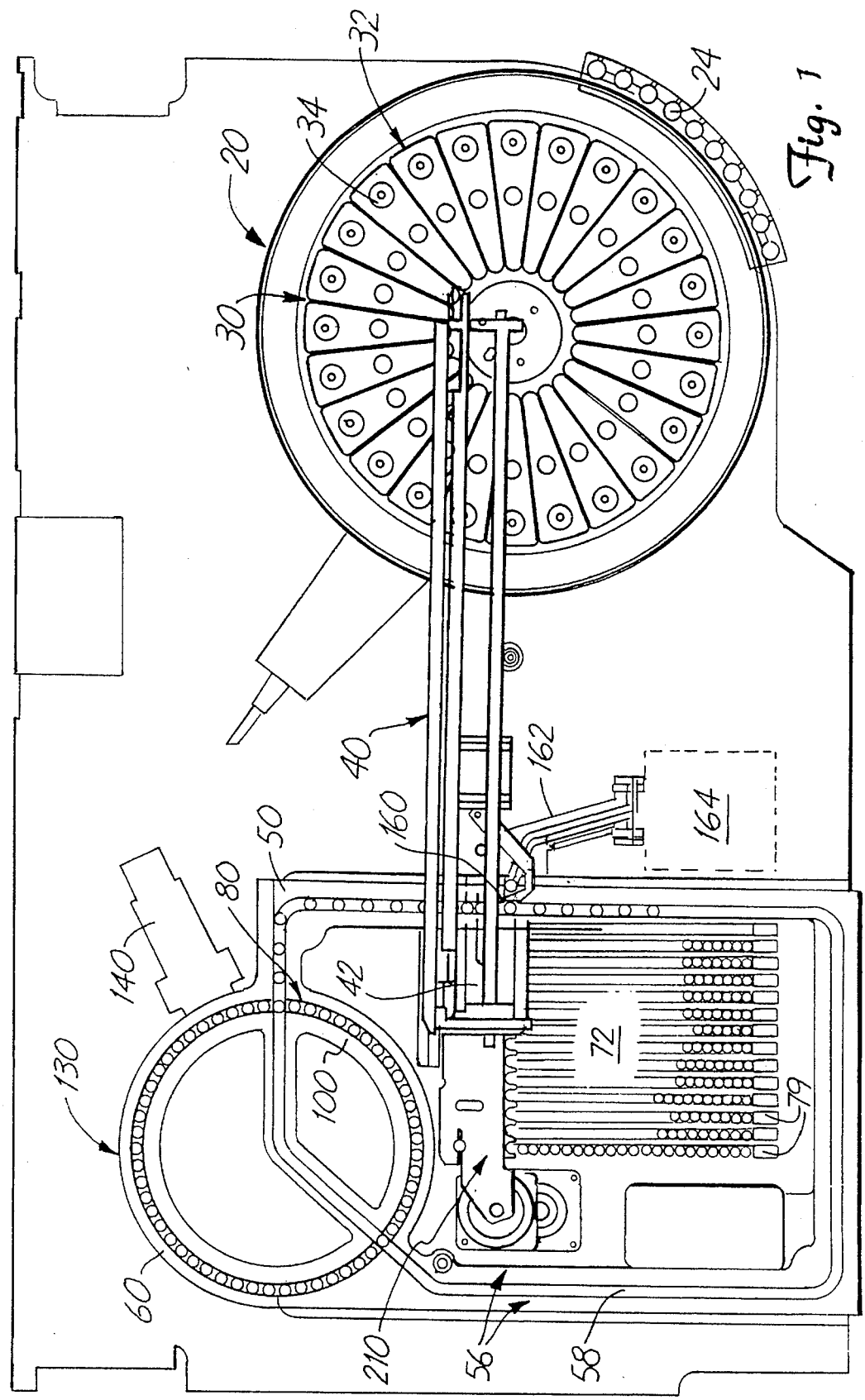
FIG. 1 is a schematic representation of a vessel transport mechanism of the invention in a chemical analyzer.

FIG. 1 schematically represents an analyzer 10 of the invention. The analyzer shown includes an assay constituents supply wheel 20, an assay constituents delivery means 40, an incubator 50, a wash wheel 60 positioned adjacent a wash station 100 and a read station 130 and various other components which can be varied as desired to achieve a suitable chemical analyzer. The overall operation and design of chemical analyzers is beyond the scope of the present discussion. However, an analyzer such as that shown in FIG. 1 is described in detail in PCT application number PCT/US93/04209, published as PCT Publication No. 93/22686 on Nov. 11, 1993, the teachings of which are incorporated herein by reference. A wide variety of other designs and arrangements of such analyzers is well known in the art and a vessel transport of the present invention can be used with any such analyzer where vessels need to be moved along a path.

The analyzer shown in FIG. 1 begins processing an analyte by using assay constituents delivery means 40 to withdraw a predetermined amount of patient sample from a sample cup and transfer it to a reaction vessel held in a vessel shuttle (210 or 210') of the invention. As indicated schematically in FIG. 1, the assay constituents delivery means 40 is adapted to access a sample cup 24 containing a patient sample, a reaction vessel 52 and each of the wells 34 of a selected reagent pack 32. In FIG. 1, the assay constituents delivery means is represented as a single probe 42. If desired, a plurality of probes may be employed, e.g., with one probe dedicated to transferring patient sample and one or more probes used to transfer reagents.

The incubator 50 desirably has an incubator belt 54 which is designed to transport one or more reaction vessels in any direction along a predetermined path 58. Although the schematic depiction of FIG. 1 shows reaction vessels only along a portion of the circumference of the incubator, the incubator desirably is adapted to carry vessels along its entire circumference. The reaction vessels are adapted for movement together within the incubator, but they should be relatively easily placed onto or removed from the belt. In one preferred embodiment described below in connection with FIGS. 3–9, the belt 54 is adapted to releasably receive and engage each of the vessels for movement therewith.

The incubator desirably includes a housing which includes a pair of parallel walls 56 which are spaced apart from one another to define the incubator path 58. The incubator also includes a floor for supporting the bottom of the reaction vessels 52 and means for controlling temperature (not shown). As best seen in FIGS. 4–7, the incubator belt 54 desirably comprises an elongate, endless tape 62 which extends along the entire length of the incubation path 58 at a position disposed generally above the floor of the incubator. This tape should be flexible so that it may travel around the corners of the incubation path. The tape is adapted to carry a series of spaced-apart carriers 64 along its length. Each carrier includes a connector 66 for connecting the carrier to the tape 62. The carriers may be removably attached to the tape so that they can be easily replaced without having to replace the entire incubator belt 54.

The carrier 64 also includes a pair of spaced, parallel fingers 68 which depend downwardly from the connector 66. These fingers are spaced apart from one another a distance slightly greater than the width of a reaction vessel 52 so that a reaction vessel may pass between the fingers without undue resistance. The spacing between the fingers should not be too great, however, because the fingers are positioned to help support a reaction vessel in a generally vertical position, as shown. The parallel walls 56 of the incubator are desirably similarly spaced to provide additional support to the reaction vessels. Each reaction vessel 52 rests upon the floor of the incubator, and the parallel fingers 68 of the incubator belt carrier and the parallel walls 56 support the vessel in a generally vertical position as it is moved along the incubation path.

In the embodiment shown in FIG. 1, a vessel transport mechanism, or vessel shuttle, interacts with the incubator 50 at the incubation transfer station 160. At the incubation transfer station 160 the reaction vessel may be transferred to or from the incubator belt or it may be transported to a waste chute, as described below. In a first embodiment of the invention, illustrated in FIGS. 2–7, the vessel shuttle 210 conveys a reaction vessel to or from the incubation transfer station 160 and to or from the incubator belt 54 (described below). Although the vessel shuttle is described in connection with the automated analyzer shown in FIG. 1, it should be apparent that it may be adapted for use in any automated analyzer where vessels or other materials must be moved from one position to another.

Figure 2:
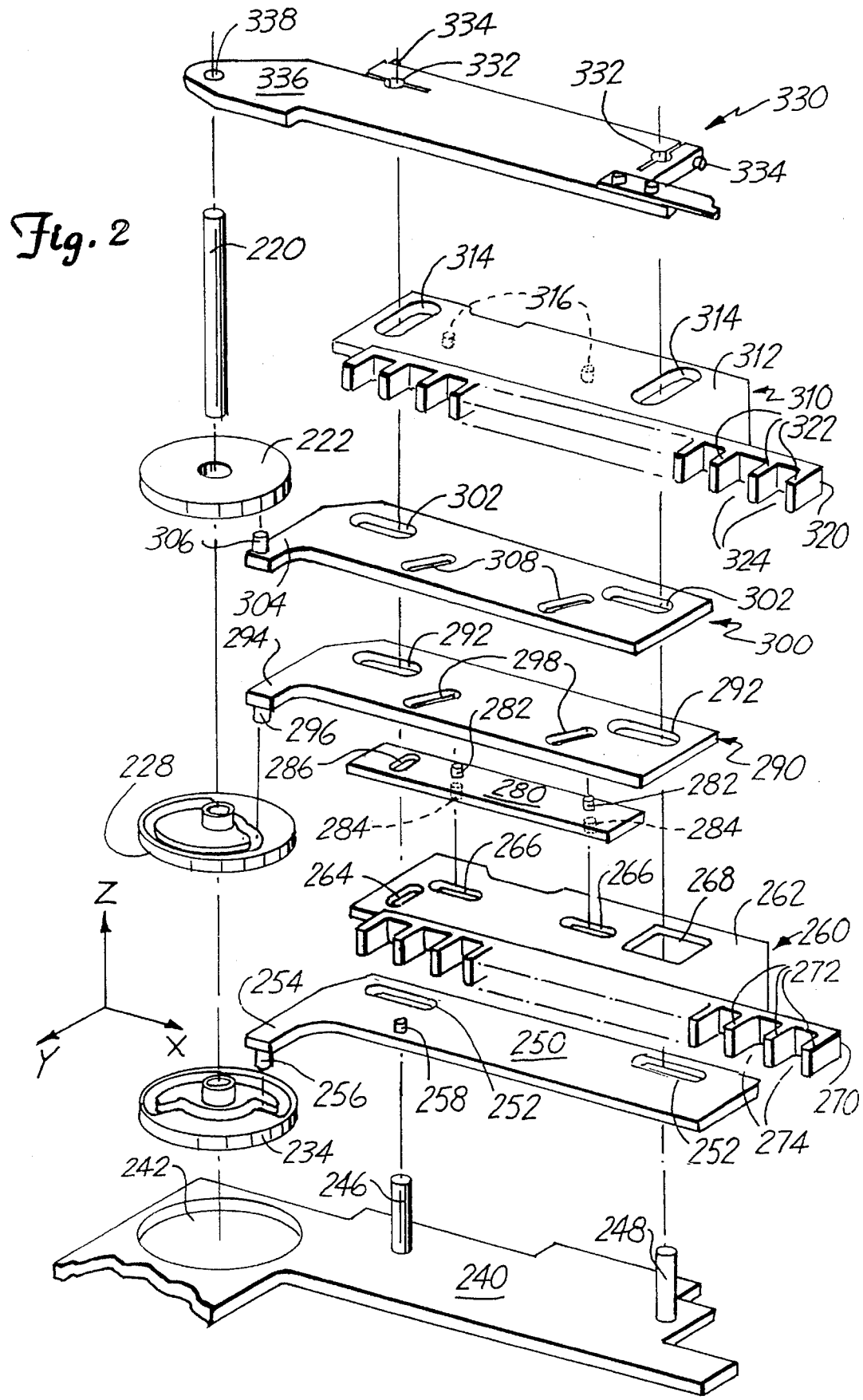
FIG. 2 is an exploded perspective view of one embodiment of a vessel transport mechanism in accordance with the present invention.

FIG. 2 shows an exploded perspective view of one embodiment of a vessel shuttle in accordance with the present invention. This vessel shuttle 210 generally includes a series of cams which are used to actuate associated plates, two of which include fingers for engaging and moving vessels stepwise along the generally linear shuttle path.

More particularly, the vessel shuttle 210 includes a driver having a drive shaft 220 with a series of cams 222, 228 and 234 affixed to the drive shaft 220 for rotation therewith. The drive shaft 220 is operatively connected to a driving mechanism, such as a motor, (not shown) which imparts rotation to the shaft. The driving mechanism may be of any desired type, but a motor which allows relatively precise control over the movement of the drive shaft, e.g., an electric stepper motor or the like, is preferred. As illustrated in FIGS. 3A–3C, each of the cams 222, 228 and 234 is desirably of the type commonly referred to as a "face cam" and includes a recessed track (224, 230 and 236, respectively). As explained in more detail below, these tracks are adapted to receive a cam follower of an associated plate of the vessel shuttle and serve to move the plate as the drive shaft 220 is rotated.

As shown in FIGS. 3A–3C, each of the cams 222, 228 and 234 include a hub (226, 232 and 236, respectively) for receiving the drive shaft 220. In one preferred embodiment, each of these ports 226, 232 and 234 includes a keyway recess (not shown). This recess is adapted to receive a mating projection (not shown), referred to as a "key", on the drive shaft 220. This serves to spline the cams to the drive shaft to ensure that they rotate together without slipping.

As shown in FIG. 2, the vessel shuttle 210 includes a base plate 240 as the lowermost plate of the beam. This base plate may include a cam-receiving orifice 242 through which the drive shaft 220 may pass. If so desired, an electric motor or other drive means (not shown) may be positioned beneath the base plate 240 and directly attached to the drive shaft. Alternatively, the motor may be disposed to the side and be connected to the drive shaft by means of gears (not shown) which may extend into the orifice 242.

The base plate also includes a pair of upstanding rods 246, 248. As explained in more detail below, at least one of these rods optimally passes through all of the plates and serves to align the plates with one another and help define the direction in which the plates can move. These rods 246 and 248 are desirably oriented generally perpendicularly to the substantially horizontally disposed plate 240, i.e., they desirably extend upwardly in the direction of the z-axis shown in FIG. 2.

Moving upwardly in the exploded view shown in FIG. 2, the next plate in the vessel shuttle 210 is the first drive plate 250. This first drive plate is desirably a relatively thin, planar plate which may be generally rectangular in shape. The plate desirably includes a pair of slots 252 which are adapted to receive the rods 246, 248 of the base plate therethrough. The slots are desirably sized to permit very little or no movement of the first drive plate in the direction of the y-axis, but permit lateral movement of the plate in the direction of the x-axis.

The first drive plate 250 also includes an arm 254 extending from the main body of the plate to a position adjacent the first cam 234. The arm 254 includes a cam follower 256 which is adapted to be slidably received within the track 236 of the first cam 234. As the cam 234 turns with the drive shaft 220, the cam follower 256 will slide along the track in the cam.

As best seen in FIG. 3C, the distance between the track 236 and the hub 238 of the cam varies at different angles. Since the cam follower 256 of the first drive plate is received within the track, the distance between the cam follower and the hub of the cam will change as the cam is rotated. This, in combination with the slots 252, will cause the first drive plate 250 to move back and forth in the direction of the x-axis as the cam is rotated.

The first drive plate 250 includes a pin 258 carried on the upper surface thereof. As explained in more detail below, this pin 258 operatively connects the first drive plate 250 to the first vessel carrying plate 260 and serves to move the first vessel carrying plate back and forth in the direction of the x-axis.

Moving up to the next plate in the exploded view of FIG. 2, the first vessel carrying plate 260 generally comprises a rearward plate portion 262 and a forward vessel carrying beam 270. The rearward plate portion includes a first drive slot 264 which is positioned to receive the drive pin 258 of the first drive plate 250. The first drive slot 264 should be elongate and extend rearwardly in the direction of the y-axis. The width of the slot 264 in the x-axis should only be slightly greater than that of the drive pin 258. As the first drive plate 250 is moved back and forth in the direction of the x-axis, as explained above, the drive pin 258 will engage the walls of the first drive slot 264, moving the first vessel carrying plate 260 back and forth along the x-axis. However, since the first drive slot is elongated in the direction of the y-axis, the first vessel carrying plate is free to move with respect to the first drive plate in the direction of the y-axis.

The rearward plate portion 262 of the first vessel carrying plate also includes a pair of elongate second drive slots 266. These second drive slots extend laterally in the direction of the x-axis. As explained more fully below, these second drive slots are adapted to receive pins 284 which drive the first vessel carrying plate 260 forwardly and rearwardly in the direction of the y-axis.

The rearward plate portion 262 of the first vessel carrying plate also includes an idler port 268 for receiving the second rod 248 of the base plate 240. This idler port 268 should be large enough to permit the first vessel carrying plate to move freely in both the x-direction and y-direction. As made more clear below in connection with the schematic drawings of FIGS. 4–7, the idler port 268 is desirably generally rectangular in shape to permit the first vessel carrying plate 260 to operate as outlined in connection with those figures.

The rearward plate portion 262 should be narrow enough to avoid any abutting contact with the first rod 246 of the base plate. If not, a second idler port (not shown) could be provided for receiving the first rod 246. Although the rearward plate portion 262 could be made narrow enough to fit between the first and second rods 246, 248 and avoid the necessity of including even a single idler port 268, it is preferred that at least one idler port be used to simplify assembly of the vessel shuttle 210 by using at least one of the rods 246, 248 to align the first vessel carrying plate with the other plates of the vessel shuttle.

As noted above, the first vessel carrying plate 260 includes the first vessel carrying beam 270. This vessel carrying beam is disposed along the forward edge of the rearward plate portion 262 and may be affixed thereto by any suitable means, such as by welding or by integrally forming the plate 262 and beam 270. Whereas the plate portion 262 is desirably relatively thin, the beam 270 should be somewhat thicker so that it can support vessels, as explained below.

The first vessel carrying beam 270 generally includes a series of forwardly extending fingers 272. These fingers are desirably elongate, generally planar members which extend in the y-axis direction and are spaced apart along the length of the vessel carrying beam. The spaces between the fingers define vessel-receiving recesses along the length of the beam 270. (In FIG. 2, some of the fingers and recesses along the beam have been omitted to simplify the drawing, but it should be understood that the fingers and recesses desirably extend along the entire length of the beam 270.) As explained below in connection with FIGS. 4–7, these vessel-receiving recesses are adapted to supportingly receive a lower portion of a vessel.

The next-adjacent plate moving upwardly in FIG. 2 is the translation plate 280. This translation plate includes a pair of upper pins 282 and a pair of lower pins 284. The lower pins 284 are carried on the lower surface of the translation plate and one such pin is adapted to be received in each of the second drive slots 266 in the first vessel carrying plate. As the second drive slots are elongate and extend in the x-axis direction, the lower pins are free to move with respect to the first vessel carrying plate 260 in the x-axis but any movement of the lower pins 284 in the y-axis direction will cause the vessel carrying plate 260 to move in that direction as well.

As explained more fully below, the upper pins 282 of the translation plate are received within translation slots 298 in the second drive plate 290. The translation plate 280 includes at least one idler slot 286 adapted to receive one of the upstanding rods 246, 248 of the base plate. In the embodiment shown, the translation plate includes one idler slot 286 which is adapted to slidingly receive the rod 246, but two idler slots could be provided. This idler slot is desirably elongate in the direction of the y-axis to restrict movement of the translation plate to movement substantially corresponding to the y-axis of FIG. 2.

The next plate in the sequence illustrated in FIG. 2 is the second drive plate 290. This second drive plate includes a pair of idler slots 292 adapted to receive the rods 246, 248 of the base plate and to help align the second drive plate with the rest of the assembly when the vessel shuttle 210 is being put together. Additionally, these idler slots 292 extend along the x-axis, restricting motion of the second drive plate to movement substantially coinciding with the x-axis.

The second drive plate includes an arm 294 which extends from the body of the plate to a position adjacent the second cam 228. Similar to the first drive plate 250 detailed above, the second drive plate includes a cam follower 296 on the arm 294. This cam follower 296 is adapted to be received within the track 230 on the second cam.

Much like the first drive plate 250 and the first cam 234, as the second cam 228 is rotated by the drive shaft 220, the distance between the cam follower 296 and the hub 232 of the cam will vary. This in turn causes the second drive plate to move in the direction of the x-axis. The movement of this plate is desirably substantially limited solely to movement in the x-axis direction by the rods 246, 248 received within the idler slots 292.

The second drive plate 290 also includes a pair of translation slots 298. As noted above, these slots 298 are adapted to receive the upper pins 282 of the translation plate 280. These translation slots 298 are elongate and are oriented at an angle to both the x-axis and the y-axis. The slots 298 desirably are not substantially wider than the pins 282 of the translation plate. The movement of the translation plate is restricted by the rod 246 in the idler slot 296, which is elongate in the y-axis direction and thus limits motion of the translation plate to motion substantially coinciding with the y-axis. Accordingly, as the second drive plate 290 is moved by the cam 228 in the direction of the x-axis, the angle of the translation slots 298 will cause the translation plate 280 to slide back and forth generally along the y-axis.

These translation slots therefore serve to effectively "translate" motion of the second drive plate, which is restricted to the x-axis, to movement of the translation plate 280 generally along the y-axis. The lower pins 284 on the lower surface of the translation plate 280 are free to slide within the second drive slots 266 of the first vessel carrying plate 260, but are substantially prevented from moving in the direction of the y-axis with respect to that plate. Accordingly, the translation slots 298 and the translation plate 280 serve to move the first vessel carrying plate 260 back and forth along the y-axis as the second drive plate 290 is moved back and forth along the x-axis by the cam 228.

In the embodiment shown in FIG. 2 the plate disposed just above the second drive plate 290 is a third drive plate 300. This third drive plate 300 includes idler slots 302 for receiving the rods 246, 248 of the base plate 240, which restricts motion of the third drive plate to movement substantially along the x-axis. The third drive plate includes an arm 304 and a cam follower 306 carried by the arm which is adapted to ride within the track 224 of the third cam 222. Once again, as the cam 222 rotates with the drive shaft 220, the distance between the cam follower 306 and the hub 226 of the cam will change, urging the third drive plate back and forth in the x-axis direction.

The third drive plate 300 also includes a pair of translation slots 308. Much like the translation slots 298 of the second drive plate 290, the drive slots 308 of the third drive plate are oriented at an angle with respect to both the x-axis and the y-axis. Pins 316 carried on the lower surface of the second vessel carrying plate 310 are received within the translation slots 308 in much the same fashion that the pins 282 are received within the translation slots 298 of the second drive plate.

The angles of the translation slots 298 and 308 may be varied as desired in order to effectuate the desired degree of motion in the y-axis. In the embodiment shown, both pairs of translation slots 298, 308 are oriented at about a 30° angle with respect to the x-axis and, therefore, at about a 60° angle to the y-axis. It should be understood, though, that this angle may be varied as necessary to achieve more or less movement of these plates in the direction of the y-axis.

The next plate moving upwardly in FIG. 2 is the second vessel carrying plate 310. This second vessel carrying plate includes a rearward plate portion 312 and a second vessel carrying beam 320. The rearward plate portion includes a pair of elongate idler slots 314, with one slot being adapted to receive each of the rods 246, 248 attached to the base plate 240. These idler slots 314 serve to align the second vessel carrying plate 310 with the rest of the plates and to restrict movement of this plate to movement substantially coinciding with the y-axis shown in FIG. 2. Thus, as the third drive plate 300 moves back and forth along the x-axis under the action of the cam 222, the pins 316 on the bottom surface of the rearward plate portion 312 will ride back and forth along the length of the translation slots 308 of the second drive plate. This movement, in combination with the idler slots 314 of the rearward plate portion 312, will cause the second vessel carrying plate 310 to move back and forth along the y-axis as the third drive plate 300 moves laterally in the x-axis direction.

The second vessel carrying beam 320 is configured substantially the same as the first vessel carrying beam 270. In particular, the second vessel carrying beam is desirably substantially thicker than the rearward plate portion 312 of the second vessel carrying plate and includes a series of elongate, generally planar fingers 322 spaced along the length of the beam 320. These fingers in turn define a series of vessel-receiving recesses 324 spaced along the length of the beam. These recesses 324 are desirably sized and shaped to supportingly receive an upper portion of a vessel for use in the analyzer. The two vessel carrying beams 270, 320 are desirably thick enough so that the bottom edge of the second beam 320 is immediately adjacent the upper surface of the first beam 270 despite the presence of the intervening plates; this relationship is schematically illustrated in FIGS. 4–7.

The uppermost plate of the vessel shuttle 210 shown in FIG. 2 is a cap plate 330. This cap plate includes a pair of spaced-apart rod ports 332. Each of these rod ports is adapted to receive an upper portion of one of the rods 246, 248 attached to the base plate. In the embodiment shown in FIG. 2, the rod ports 332 may be tightened about the rods received therein by means of a locking screw 334 which serves to clamp the port 332 about the rod.

The cap plate 330 may also include an arm which extends laterally of the main body of the plate. This arm 336 may be provided with a hole 338 for receiving an upper portion of the drive shaft 220. The drive shaft should be free to rotate within this hole 338 and the hole may have bearings or the like on its inner surface in order to ensure the drive shaft sufficient freedom of rotation.

When the vessel shuttle 210 of the invention is assembled, each of the plates may be sequentially passed over the rods 246, 248 attached to the base plate and allowed to rest upon one another. In this fashion, each of the plates supports the others. As the plates move in response to rotation of the drive shaft 220, though, this will tend to cause friction between the plates. In order to reduce this friction and the wear which results therefrom, the plates may be coated with an abrasion-resistant material or a somewhat lubricous material such as polytetrafluoroethylene (PTFE). In one particularly preferred embodiment, small "buttons" (not shown) of Delrin (an acetal resin manufactured by E.I. DuPont de Nemours & Company) or a similar polymeric material are applied to the upper and lower surfaces of each of the plates. These Delrin buttons serve to both reduce friction between the plates and wear sacrificially to reduce wear on the plates themselves. In order to maintain a relatively compact design, the Delrin buttons are optimally relatively thin.

Figure 3:
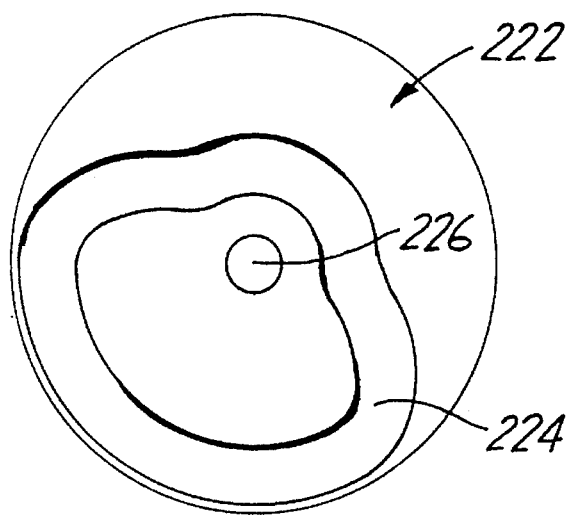
FIGS. 3A–C are top isolation views of the cams used to drive the vessel transport of FIG. 2.
Figure 3:
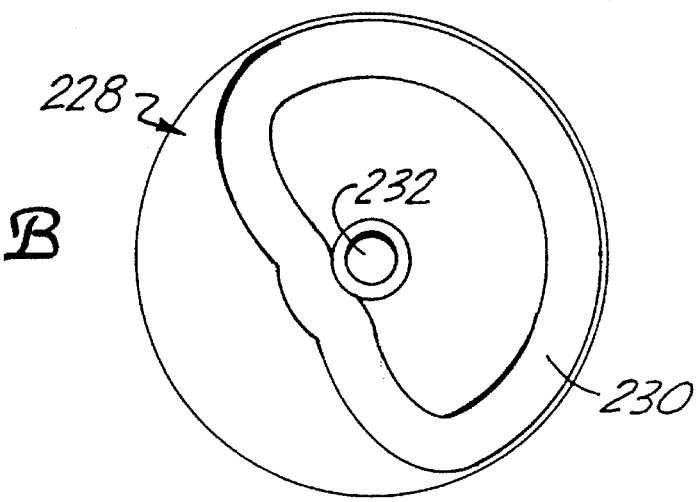
Figure 3:
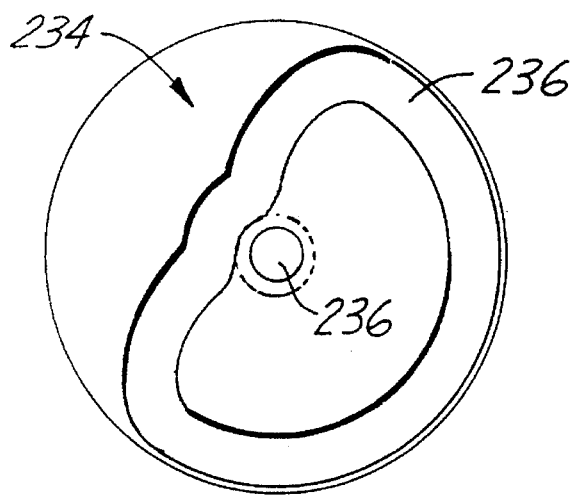

FIGS. 3A–3C depict the cams 234, 228 and 222 which drive the first, second and third drive plates (250, 290 and 300), respectively. The shape of the track in each of these cams should be designed to effectuate the desired movement of the first and second vessel carrying plates (260 and 310, respectively), as explained below in connection with FIGS. 4–7. Although tracks shaped substantially as shown in FIG. 3 have been found to work well, it should be understood that the shapes of these tracks could be adjusted somewhat yet yield the desired motion of the first and second vessel carrying plates. It is desirable, however, to ensure that the plates are not suddenly jerked in one direction or another as this may cause the contents of the vessels supported by the vessel carrying beams 270, 320 to splash either out of the vessels or up onto the vessel walls. Instead, the tracks should present a relatively gradual rate of change in the radius between the track and the hub of the cam. This will avoid any sharp discontinuities in acceleration of the vessels and minimize splashing of the fluids therein.

In the configuration shown in FIG. 2, the vessel transport 210 of the invention can be removed as a single unit without having to disassemble the entire unit. In a preferred embodiment, the motor (not shown) which drives the drive shaft 220 is permanently affixed to the rest of the apparatus and interacts with the drive shaft by means of gears. This permits the entire unit, including the cams and the drive shaft, to be replaced quickly and easily by simply removing the entire vessel shuttle assembly and replacing it with a new vessel shuttle assembly. This limits down time of the apparatus if there is a malfunction.

FIGS. 4–7 schematically illustrate operation of the vessel shuttle 210 set forth above. The vessel shuttle shown in FIGS. 4–7 supports a plurality of vessels 52 which rest upon a floor 73, which is optimally horizontally aligned with the floor of the incubator 50 so that as a vessel is transferred onto the incubator there is no sharp discontinuity which could cause jarring of the vessel, causing the contents thereof to splash and possibly affect the results of the test being conducted. In a preferred embodiment, the floor 73 of the vessel shuttle is integrally formed with the floor of the incubator.

At all times, at least a portion of each vessel on the vessel shuttle 210 will be received within and supported on three sides by a vessel-receiving recess 274 or 324 of the first or second vessel carrying beams 270 or 320, respectively. The vessels will be supported on the other side by additional vessels which have not yet been loaded and remain in the new vessel loader (72 in FIG. 1).

Figure 4:
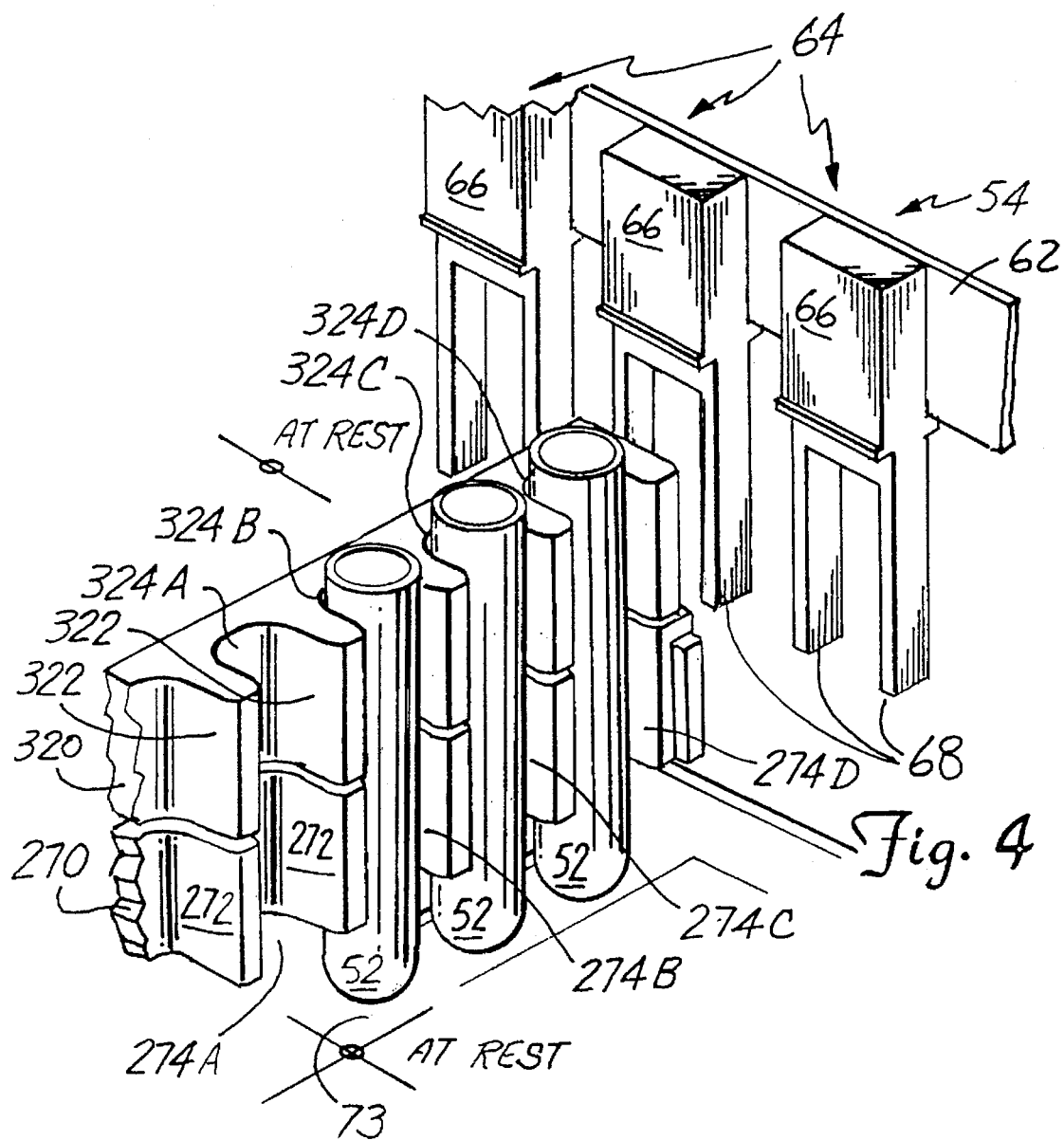
FIGS. 4–7 are perspective isolation views of the vessel transport of FIG. 2 schematically illustrating operation of the vessel transport.

FIG. 4 illustrates the "rest" or default position of the vessel shuttle 210. In this position, all of the fingers of the two vessel carrying beams are substantially vertically aligned with a finger on the other beam. In particular, the vessel-receiving recesses 324A–324D of the second vessel carrying beam 320 are aligned with a recess 274A–274D of the first vessel carrying beam 270 bearing the same letter designation in FIGS. 4–7. In this position, all of the vessels loaded into the vessel shuttle 210 are supported by both the first and second vessel carrying beams. When in this position, a vessel in the recesses labeled 324D and 274D is in position for access by the assay constituents delivery means 40 and assay constituents, such as reagents and patient samples, can be added to the vessel.

Figure 5:
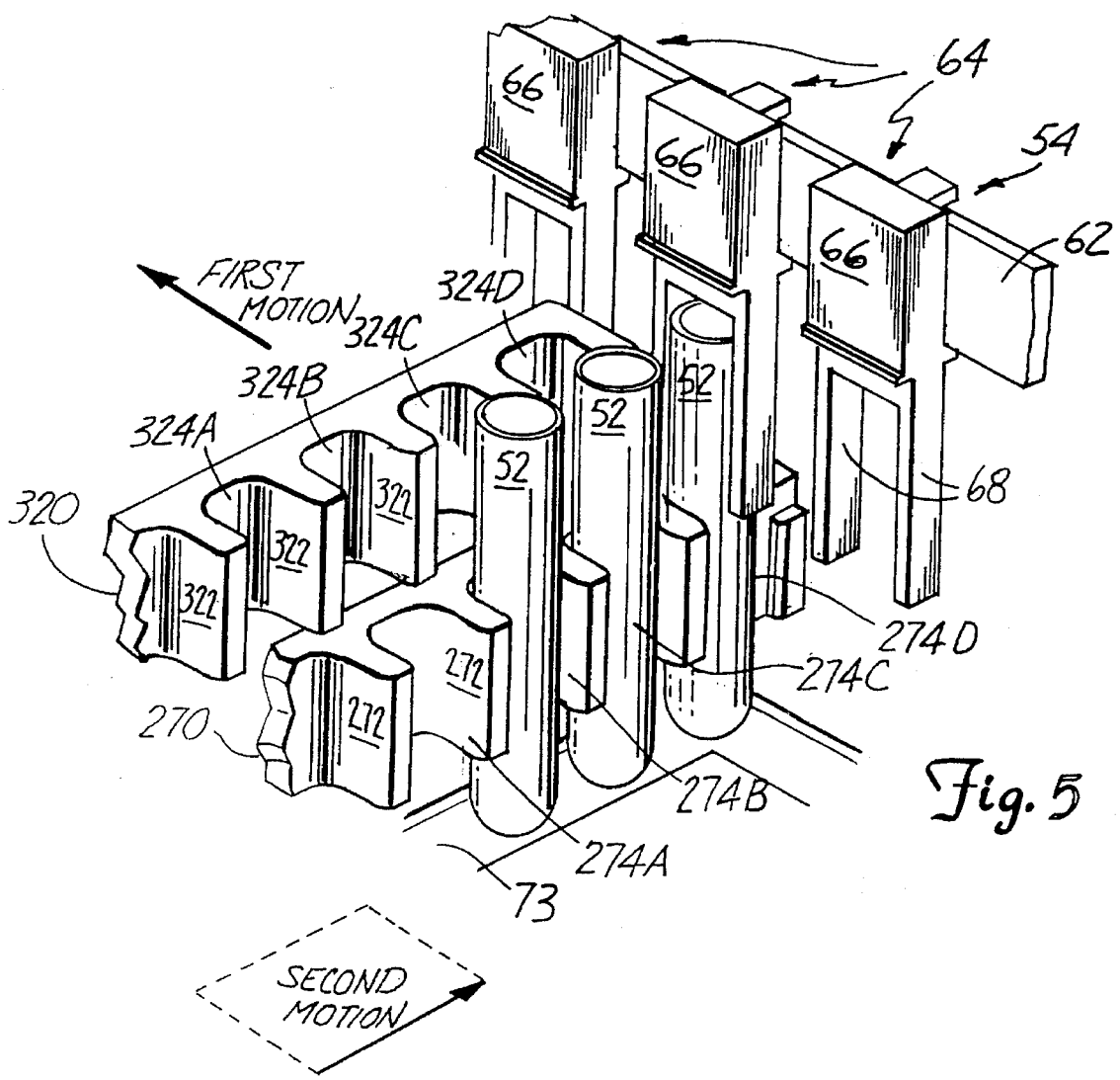

FIG. 5 illustrates the first and second motions of the two vessel carrying beams used to advance a vessel from the vessel shuttle onto the incubator 50. First, the second vessel carrying beam 320 is moved rearwardly (i.e., along the y-axis of FIG. 2). As explained above in connection with FIG. 2, this is accomplished by moving the third drive plate 300 laterally along the x-axis via cam 222. The second vessel carrying beam 320 should be retracted sufficiently so that the fingers 322 are retracted behind the rearward edges of the vessel-receiving recesses 274 of the first vessel carrying beam.

As the drive shaft 220 continues to rotate, the first cam 234 moves the first drive plate 250 to the right along the x-axis, thereby moving the first vessel carrying beam 270 to the right. The first vessel carrying beam is moved one "space" to the right, i.e., about the width of one vessel-receiving recess and one finger, as illustrated in the drawings. After this second motion of the vessel shuttle, the first beam 270 will extend into the path of the incubator 50, disposing the vessel carried by the outermost vessel-receiving recess 274D between the fingers 68 of a carrier 64 of the incubator.

Figure 6:
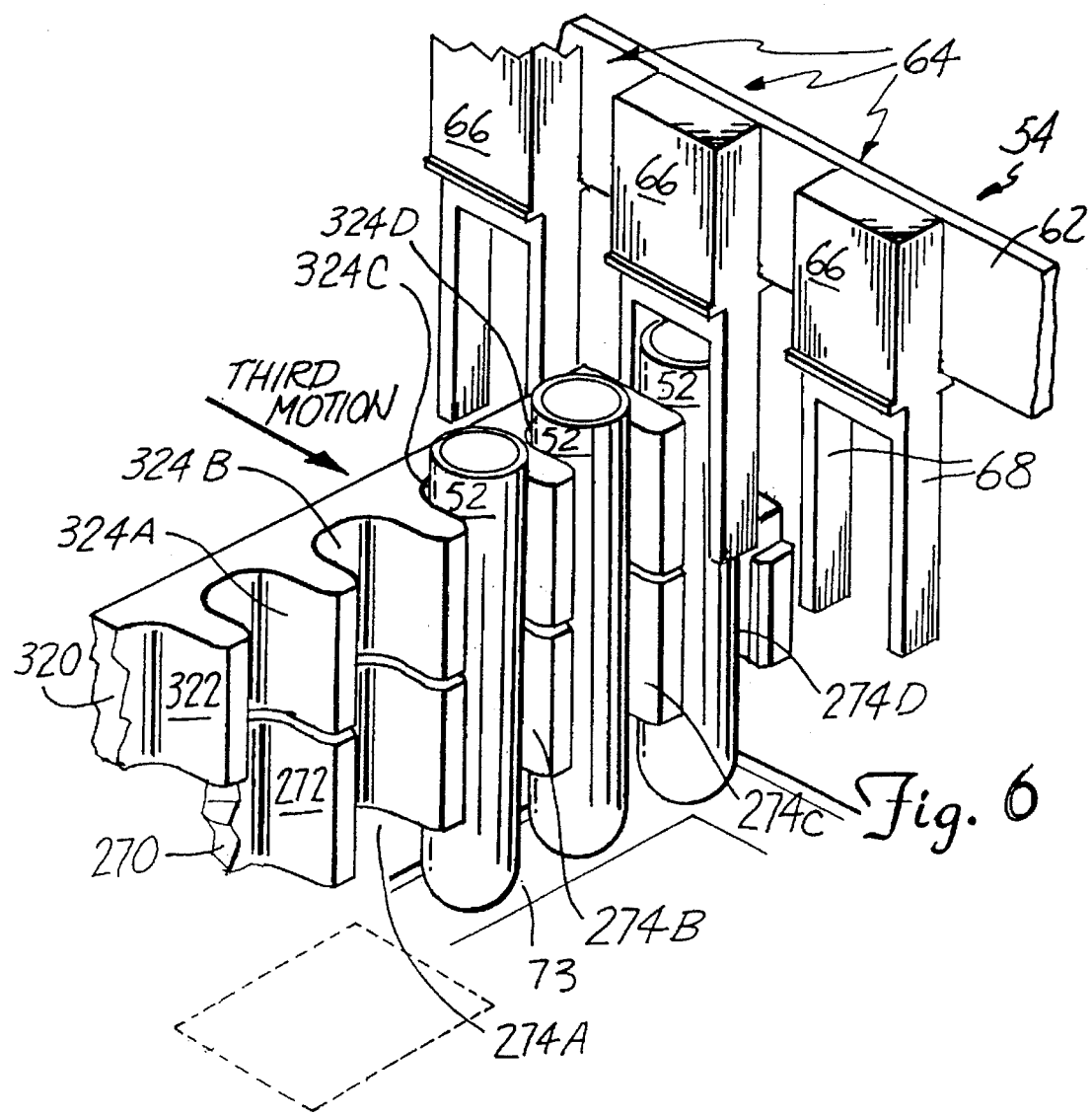

As illustrated in FIG. 6, the second vessel carrying beam 320 may then be urged forwardly again (by the action of the third drive plate 300) so that an upper portion of each of the vessels will be received within a recess 324 on that beam. It should be noted that the vessels have been indexed forward one position along this second vessel carrying beam such that the vessel which was initially in recess 324D in FIG. 4 is now disposed within a carrier 64 of the incubator and the vessel shown in recess 324D in FIG. 6 was originally in recess 324C in FIG. 4.

Figure 7:
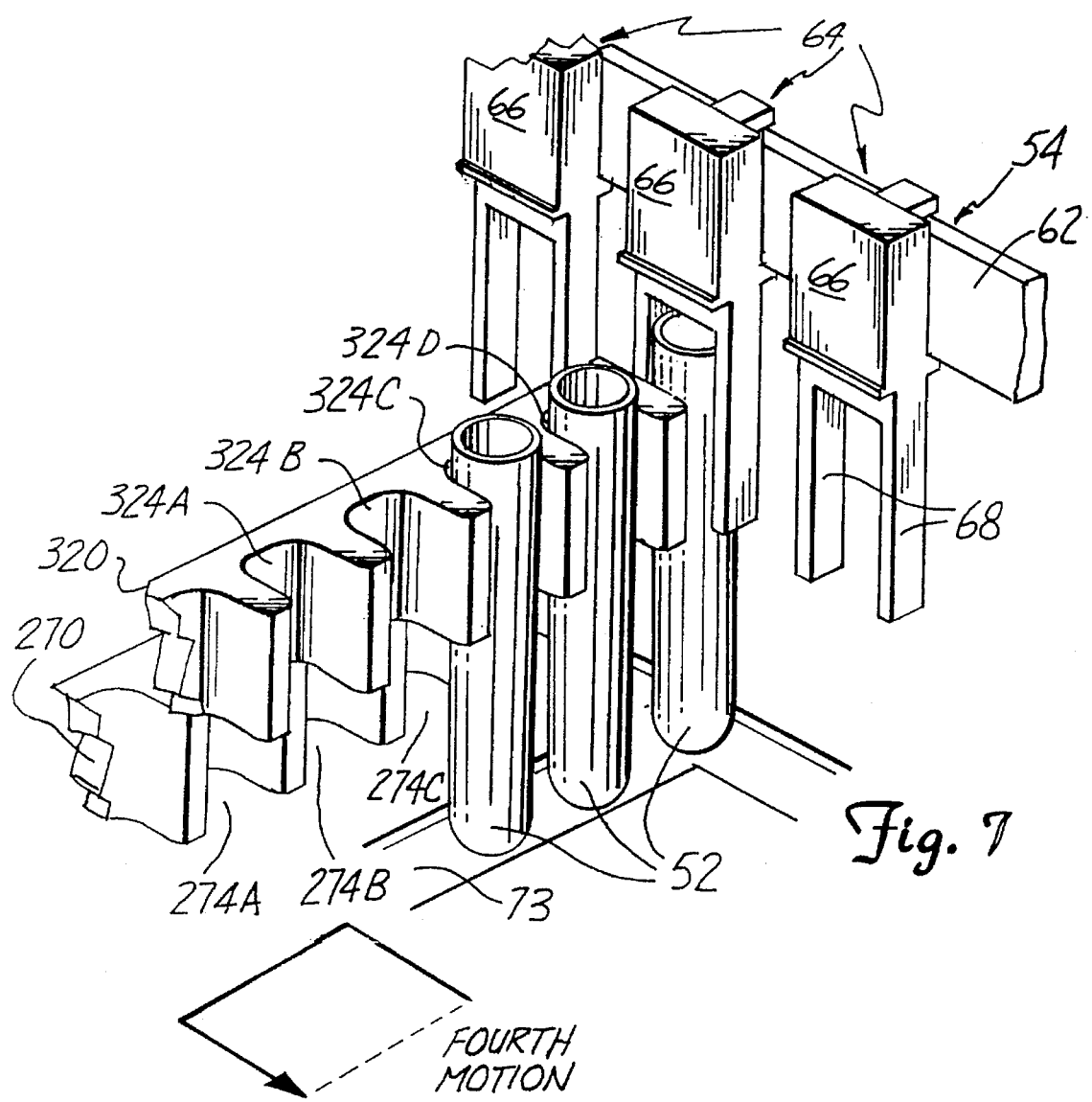

FIG. 7 shows the fourth and final motion of the vessel shuttle 210 used to index vessels forwardly. In this motion, the first vessel carrying beam 270 is retracted rearwardly (in the direction of the y-axis in FIG. 2), leaving the vessels supported by the floor 73 and the fingers 322 of the second vessel carrying beam. As explained above in connection with FIG. 2, such movement of the first vessel carrying plate 260 is accomplished by the coaction of the second drive plate 2990 and the translation plate 280. The first beam 270 should be retracted so that its fingers 272 are disposed behind the vessels. The first vessel carrying beam may then be retracted laterally, i.e., to the left in FIG. 7 (along the x-axis of FIG. 2). As the final step of this last motion, the first vessel carrying beam 270 is moved forwardly (along the y-axis of FIG. 2).

This places the first and second beams 270, 320 in their rest or default position, illustrated in FIG. 4. As shown in FIG. 7, once the fourth motion of the vessel shuttle is completed and the first beam 270 is returned to its original position, the outermost vessel on the vessel shuttle in FIG. 4 (i.e., the vessel received in recesses 274D and 324D in that Figure) has been transferred onto a carrier 64 of the incubator and the contents thereof can begin processing.

As illustrated schematically in FIGS. 4–7, the first vessel carrying plate 260 (with its associated beam 270) moves generally rectilinearly both generally parallel to and generally perpendicularly to the direction of travel of the vessels along the shuttle path. The first vessel carrying plate therefore moves in a generally rectangular path, following this rectangular path in a generally counterclockwise direction in FIGS. 4–7 to advance a vessel onto the incubator.

As outlined above, it can be seen that the vessel shuttle 210 is adapted to move vessels stepwise, i.e. in discrete steps, along a linear path. This path has an end adjacent the path of the incubator. This stepwise advancement of vessels is accomplished by cooperative movement of the first and second vessel carrying plates and these vessel carrying plates move in planes generally parallel to one another. Furthermore, each of the plates are adapted to move between a forward position wherein a vessel is supportingly received in its recesses and a rearward position wherein no vessel is in a recess of the plate. The plates move cooperatively such that at any given time at least one of the plates is in its forward position to support the vessels 52 along the path of the vessel shuttle 210.

Furthermore, it can be seen by reference to FIGS. 4–7 that at the end of an indexing movement of the vessel shuttle, (i.e. the full cycle of movement set forth above), the first and second vessel carrying plates return to the same position they were in at the beginning of the movement. In other words, the first and second vessel carrying plates move cooperatively with respect to one another so that vessels are moved along the path of the shuttle with no net motion of the carrying plates. This is in contrast to prior art systems such as chains or moving floors, which follow a closed path and move along the path with the vessels.

The vessel shuttle 210 of the invention is adapted to hold a vessel in position for access by the assay constituent means 40 for the addition of reagents or other fluids, move a reaction vessel onto or off of the incubator, and discard a waste vessel into the waste chute (explained below). One particularly advantageous aspect of the vessel shuttle of the invention is that the vessel shuttle can, in one motion, position a new vessel for access by the assay constituent delivery means, load a vessel onto the incubator and discard a spent vessel on the incubator. This combines functions usually performed by two or three different mechanisms into one apparatus, simplifying the overall apparatus, increasing system reliability and reducing down time for maintenance of the system, and conserving space within the analyzer.

An analyzer employing a vessel transport mechanism in accordance with the invention desirably includes a supply of new vessels to replenish vessels on the transport mechanism as they are consumed during operation of the analyzer. The new vessel loader 72 is provided adjacent the vessel chain 70 to supply new reaction vessels to the analyzer. The new vessel loader is readily accessible to an operator to permit the operator to add additional reaction vessels to the supply as the analyzer disposes of used reaction vessels.

The new vessel loader 72 desirably presents a series of essentially parallel lines of new vessels to the vessel shuttle 210, with the lines being spaced to position a new vessel in each line immediately adjacent a vessel carrying position on the vessel shuttle. The new vessel loader shown includes a series of parallel supporting walls 79 spaced to allow a vessel to slide between them while supporting the vessel in a generally vertical position. Each row of empty vessels is urged forward by a substantially vertical finger (not shown) that is slidably mounted in the floor of each row and supports the outermost (i.e., closest to the bottom in FIG. 1) empty vessel of each row. In the event no empty vessels are present in a row of the new vessel loader, the vertical finger will support a reaction vessel on the vessel shuttle 210.

Some assay protocols require "two-stage" processing, which necessitates the addition of a second set of reagents after a first incubation and washing process. The process for removing a vessel from the incubator 50 and retracting it onto the vessel shuttle 210 for the addition of the second stage reagents is substantially the reverse of the process outlined above for transferring a vessel onto the incubator. In particular, substantially the same motions illustrated in FIGS. 4–7 are carried out, but in reverse direction and reverse order.

Thus, in removing a vessel from the incubator, the first vessel carrying beam 270 is retracted rearwardly, advanced laterally (i.e., to the fight in FIGS. 4–7) and then moved forwardly. This places the vessel on the incubator at the incubation transfer station within the outer-most vessel receiving recess 274D of the first vessel carrying beam. The second vessel carrying beam 320 is then retracted rearwardly (the opposite of the motion shown in FIG. 6). This permits the first vessel carrying beam 270 to be retracted laterally, i.e., to the left in FIGS. 4–7, and the second vessel carrying beam 320 may be advanced forwardly into the position shown in FIG. 4.

Hence, while the second vessel carrying beam 320 moves only forwardly and rearwardly along the y-axis of FIG. 2, the first vessel carrying beam 270 moves rectilinearly along a generally rectangular path. Whereas the first vessel carrying beam moves in a counterclockwise fashion in advancing a vessel onto the incubator, as noted above, in retracting the vessel the first vessel carrying beam proceeds generally clockwise along this same rectangular path.

FIGS. 10–15 illustrate an alternative embodiment of the vessel shuttle 210 shown in FIGS. 2–8. Parts in FIGS. 10–15 which perform much the same function as parts in FIGS. 2–8 bear like reference numerals, with the addition of a prime ('). The number of parts in the vessel shuttle 210" of FIGS. 10–15 is significantly less than the number of parts in the vessel shuttle 210' of FIGS. 2–8. As explained in some detail below, this has been accomplished at least in part by replacing the face cams 222, 228 and 234 with an actuating gear assembly 400.

Figure 10:
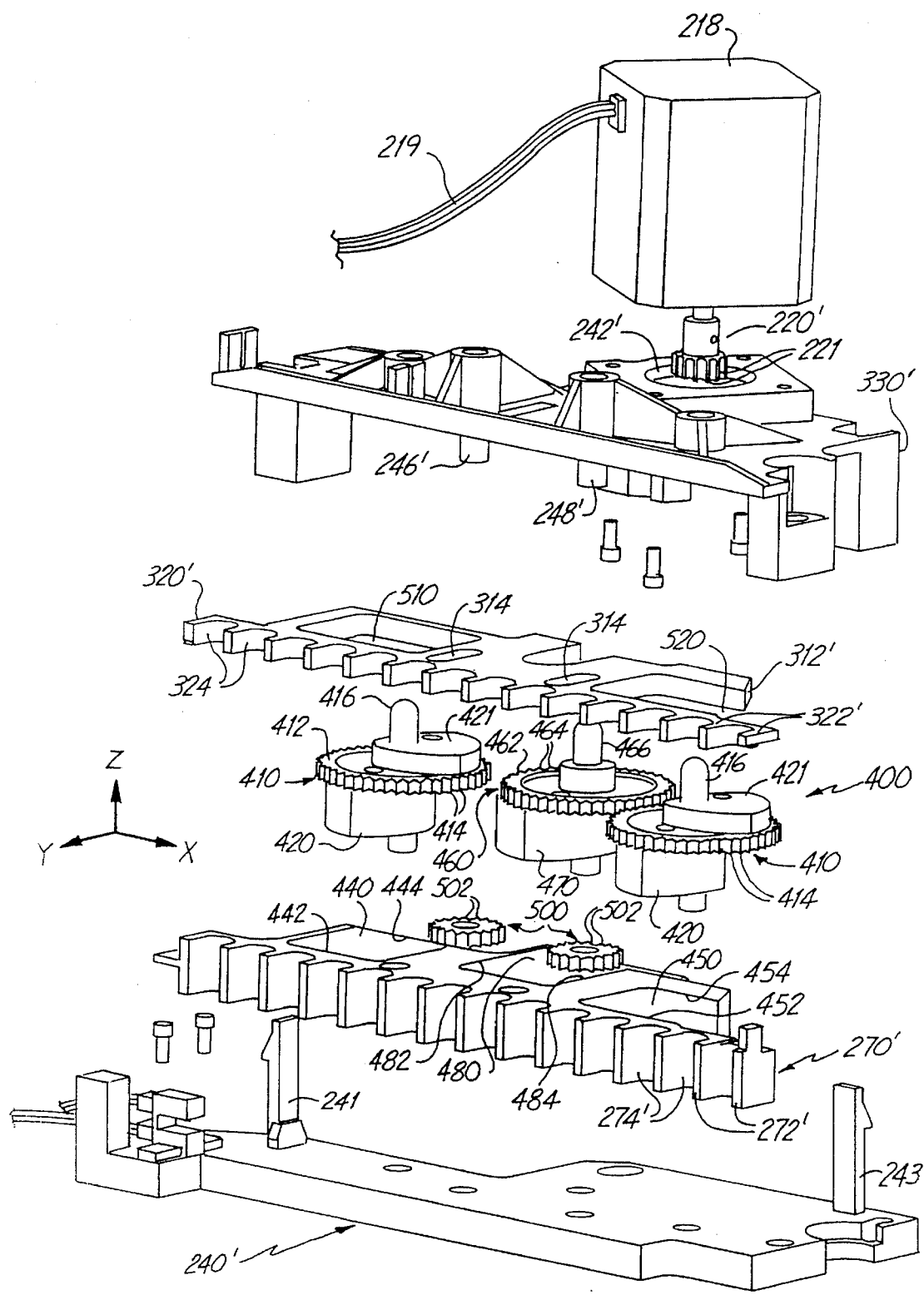
FIG. 10 is an exploded perspective view of an alternative embodiment of a vessel transport mechanism in accordance with the present invention.

Turning first to FIG. 10, the vessel shuttle 210' in accordance with this embodiment of the invention includes a base plate 240' upon which the first vessel carrying plate 260' rides. The actuating gear assembly 400 is disposed generally between the first vessel carrying plate 260' and the second vessel carrying plate 320'. The second vessel carrying plate desirably includes a pair of parallel slots extending generally in the direction of the y-axis shown in FIG. 10 to substantially restrict motion of the plate 320' to coincide with that axis. Although, as noted below, such slots may not be necessary to control the motion of the second vessel carrying plate, but such slots will assist in assembling the vessel shuttle 210', such as after the shuttle has been repaired.

A cap plate 330' covers the second vessel carrying plate and is optimally releasably attached to the base plate 240'. In the embodiment shown in FIG. 10, the base plate 240' includes a pair of resilient flanges 241, 243 which are adapted to be received in slots (not visible in the view of FIG. 10) in the cap plate 320'. By deflecting these resilient flanges 241, 243 within the slots in the cap plate, one can release the cap plate from the base plate 240' to disassemble the system for maintenance or repair.

The cap plate 330' may include an orifice 242' through which a drive gear 220' may pass to engage the actuating gear assembly 400. The gear 220' may be driven by an electric stepper motor 218 or the like. This stepper motor 218 may be connected by cables 219 to a computer control system for the analyzer to ensure that operation of this vessel shuttle 210' is synchronized with the operation of the rest of the analyzer.

The actuating gear assembly 400 of this embodiment includes at least two actuating gears 410, 460 for controlling motion of the vessel carrying plates. In the preferred embodiment shown in the drawings, the gear system optimally includes three such actuating gears, with two of the gears (both labelled 410) being substantially the same. As explained below, this will reduce twisting of the vessel carrying plates with respect to the vessel path during operation.

The actuating gear 410 has a pair of positive motion cams 420, 421 attached on either side of a flat, circular gear body 412. The gear has an upstanding central axis 416, one end of which is received in a recess provided in each of the bottom plate 240' and the cap plate 330'. The gear 410 rotates about this axis 416 and the cams are attached to the gear for rotation therewith. The two cams 420, 421 are desirably the same size and shape, but are oriented about 180° from one another about the axis 416. As explained more fully below, this will enable the two vessel carrying plates 260' and 310' to be moved generally along the y-axis shown in FIG. 10 to achieve substantially the same motion shown in FIGS. 4–7 for the vessel shuttle 210.

Figure 11:
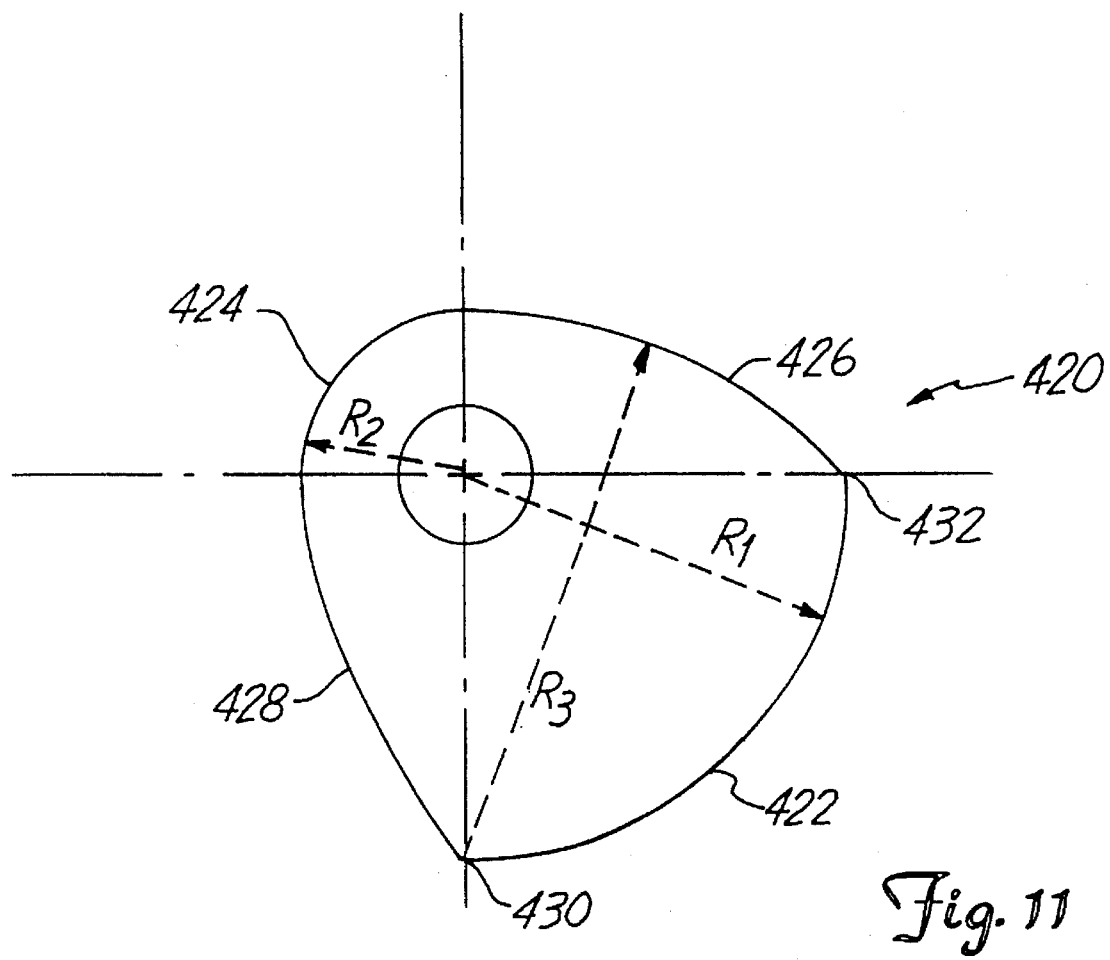
FIG. 11 is an isolation view of a cam useful in the vessel transport mechanism of FIG. 10.

Turning to FIG. 11, it can be seen that the cam 420 includes four sides or faces, 422, 424, 426 and 428, each of which occupy an arc of about 90° about the axis of the cam, which coincides with the axis 416 of the gear 410. The first two sides 422 and 424 are both concentric about the axis of the cam, with the first side 422 being spaced a radius $R_1$ from the axis and the second side 424 being spaced a radius $R_2$ from the axis. In the embodiment shown in FIGS. 10–15, the radius $R_1$ is larger than the radius $R_2$. The third side 426 of the cam is an arc having a center at a first end 430 of the first side 422 and a radius of $R_3$ about that point. As can be seen from following the center line passing through the end 430, this radius $R_3$ is equal to the sum of the first two radii $R_1$ and $R_2$. Similarly, the fourth side 428 of the cam is an arc having a center at the second end 432 of the first side 422 of the cam and has a radius equal to the radius $R_3$ of the third side 428.

The radii $R_1$–$R_3$ can be varied as necessary to achieve the desired motion of the vessel carrying plates 260' and 310'. However, these radii are directly interrelated and fixing any one of the radii or determining the exact distance the cam is to move the associated plate (referred to as the "throw" of the cam) will dictate all of the other radii of the cam. As can be seen from FIG. 11, the radius $R_3$ extends from the first end 430 to the second end 432 of the first side. This essentially defines a right triangle having its apex at the axis of the cam, two equal legs of length $R_1$ and a hypotenuse of $R_3$. Hence, the radius $R_3$ is equal to $R_1$ times the square root of 2, or about 1.414 $R_1$. Further, since $R_3$ is also equal to the sum of $R_1$ and $R_2$, $R_2$ must be equal to about 0.414 $R_1$. Finally, as will become more clear in connection with the discussion below of FIGS. 12–15, the throw of the cam 420 is equal to the difference between the cam's maximum radius from its axis ($R_1$) and its minimum radius from its axis ($R_2$), or $R_1$ minus $R_2$, which equals about 0.586 $R_1$. For example, in the embodiment of the cam 420 illustrated in the drawings, if a throw of about 0.40 inches was need, a radius $R_1$ of about 0.40/0.586=0.683 inches will be needed, which also dictates a radius $R_2$ of about 0.283 inches and a radius $R_3$ of about 0.966 inches.

The actuating gear assembly 400 of this invention also includes another actuating gear 460 which may include only a single cam 470 positioned on the lower face of the gear body 462. As explained below in connection with FIGS. 12–15, this gear and its associated cam actuate the first vessel carrying plate 260' in the direction of the x-axis shown in FIG. 10. This actuating gear 460 also includes an upstanding axis 466 which, like the axes 416 of gears 410, is received in a recess provided in each of the bottom plate 240' and the cap plate 330'. This axis 466 is substantially parallel to the axes 416 of the other two gears.

The cam 470 has a shape substantially the same as that of the cams 420, 421 attached to the other actuating gears 410. However, in the present embodiment it is desirable to move the first vessel carrying plate 260' farther in the direction of the x-axis than in the direction of the y-axis. As the cam 470 drives the x-axis motion, as detailed below, this cam is desirably larger than the other cams 420, 421. For example, the radius $R_1$ of cam 470 may be on the order of about 0.806 inches and radius $R_2$ may be on the order of about 0.334 inches, yielding a radius $R_3$ of about 1.14 inches.

The gear bodies 412 of the first two gears 410 include teeth 414 spaced around their periphery and the gear body 462 of the other actuating gear 460 also includes teeth 464 spaced about its periphery. If so desired, the teeth 464 of the third gear could be positioned to directly engage the teeth 414 of the other two gears. However, this would mean that the gears 410 would be rotating in a direction opposite the direction of the gear 460. In the embodiment shown in the drawings, two idler gears 500 are employed to ensure that the gears 410, 460 rotate in the same direction. The idler gears include teeth 502 which are adapted to engage the teeth of the central gear 460 and one of the other two gears 410.

The drive gear 220 also includes teeth 221 and these teeth are designed to engage the teeth of one of the three actuating gears 410, 460. In a preferred embodiment, the drive gear is positioned to contact the central gear 460 and positively drive that gear. Rotation of gear 460 will in turn, through idler gears 500, rotate the other two gears 410. The gear bodies 412, 462 of the three actuating gears are desirably substantially the same size so that all three gears will rotate at the same rate. This will help ensure that all three of the lower cams 420, 470 remain in phase with one another, i.e. remain in the same relative orientation about their respective axes, during operation of the vessel shuttle 210', as shown in FIGS. 12–15.

The first vessel carrying plate 260' includes three cam following orifices 440, 450 and 480 passing therethrough.

These cam following orifices are desirably rectangular in shape and are sized so that they will act with the cams 420, 470 on the gears 410, 460 to drive the first vessel carrying plate 260' rectilinearly along a rectangular path, as detailed below in connection with FIGS. 12–15.

Figure 15:
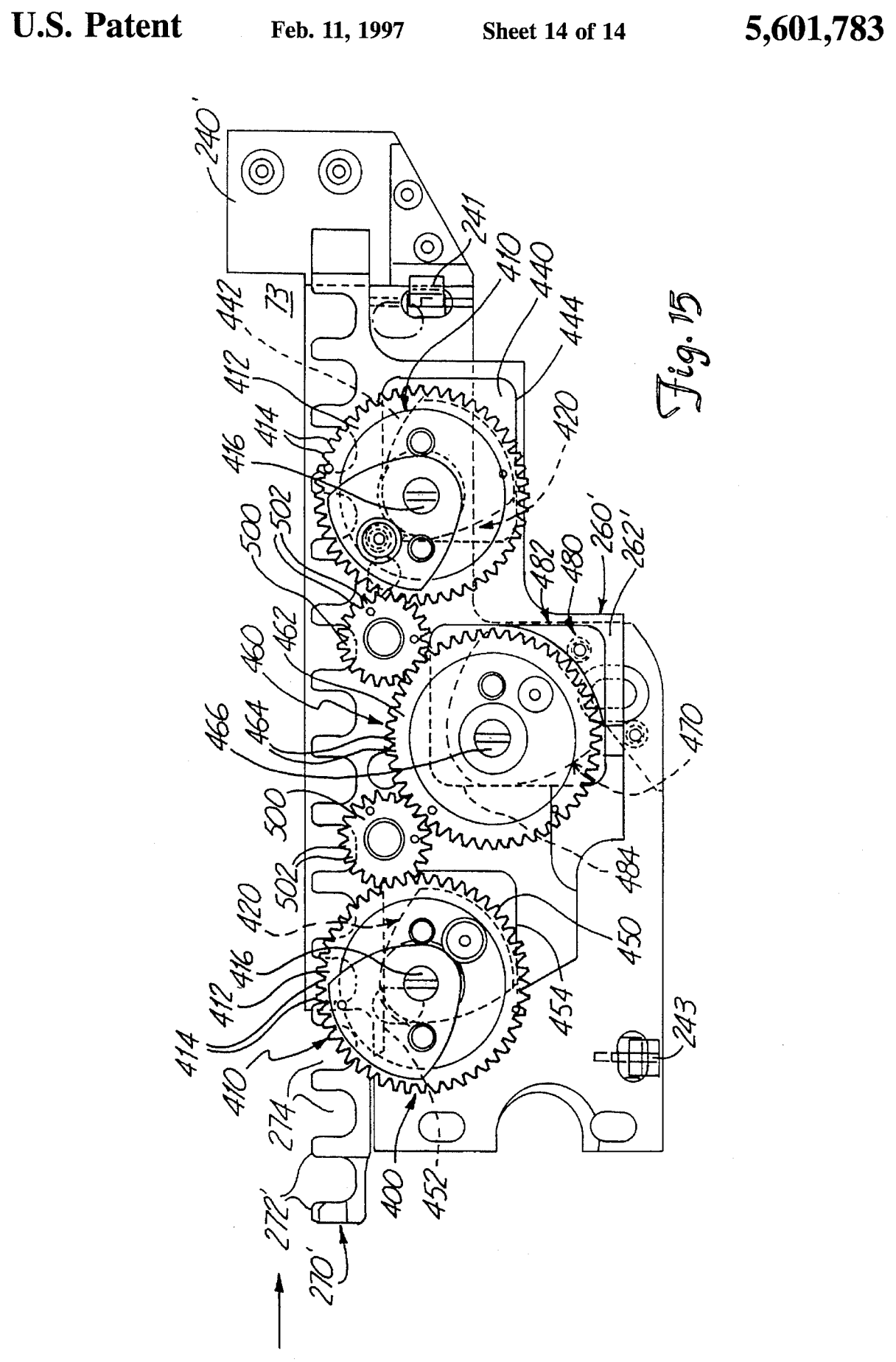

The interaction of the actuating gear assembly 400 and the first vessel carrying plate 310' is schematically illustrated in FIGS. 12–15. Briefly summarizing the movements of the carrier 260' shown in these drawings, between FIGS. 12 and 13 the carrier moves laterally in the x-axis direction, as illustrated by the arrow in FIG. 13. The carrier 260' then retracts along the y-axis to the position shown in FIG. 14, indicated by the directional arrow in that drawing. The plate then moves laterally along the x-axis in the direction opposite that noted above, as indicated by the arrow in FIG. 15. Finally, the carrier 260' returns to the "home" position shown in FIG. 12 by moving forwardly along the direction of the y-axis, as suggested by the arrow in FIG. 12. The positions of the first vessel carrying plate 260' shown in FIGS. 12–14 generally coincide with the positions of the first vessel carrying plate 260 shown in FIGS. 4, 5 and 7, respectively. (FIG. 15 illustrates a step in the motion labelled "fourth motion" in FIG. 7 and is not explicitly shown in the sequence illustrated in FIGS. 4–7.)

Figure 12:
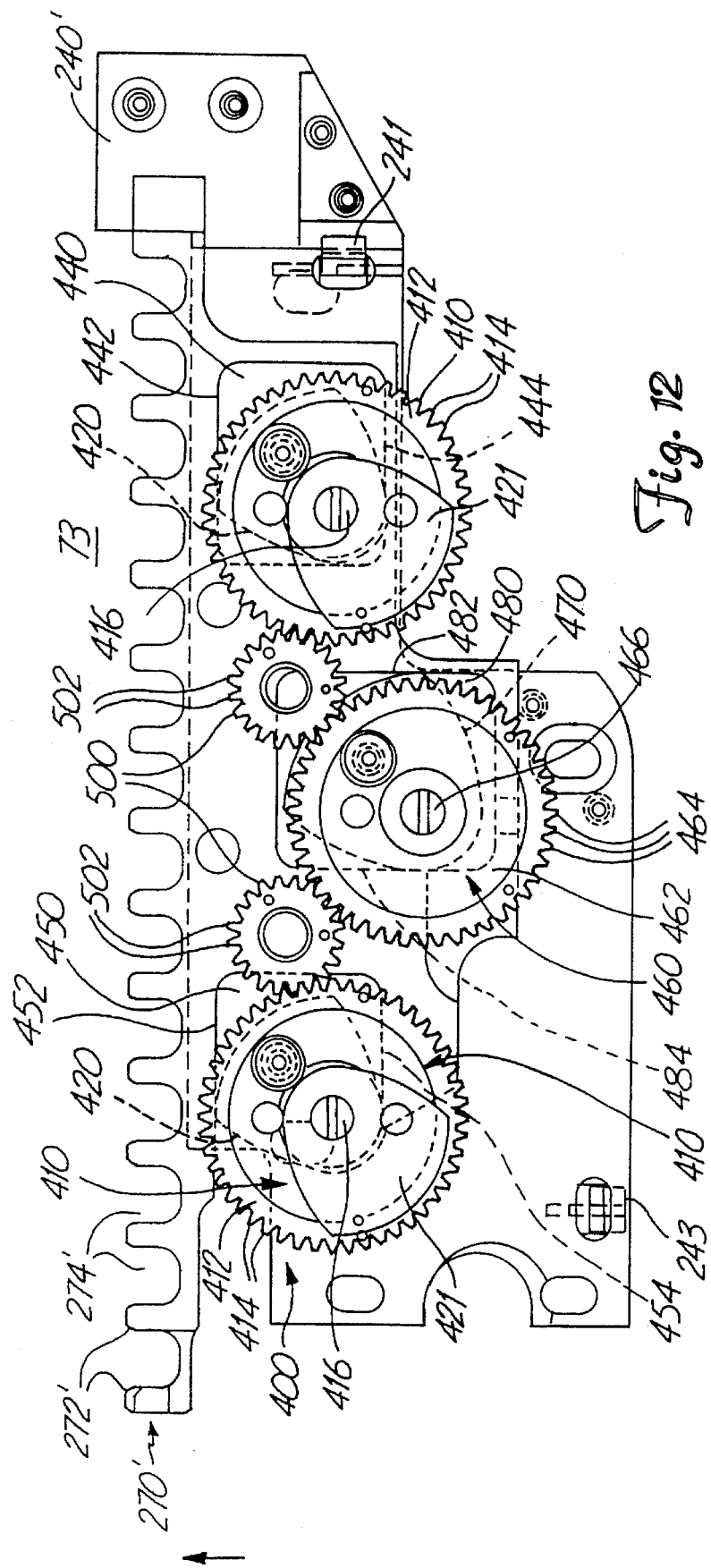

Turning first to FIG. 12, it can be seen that the cam 470 (in phantom lines) of the central actuating gear 460 is in contact with opposed walls 482 and 484 of the central cam following orifice 480. If the shape of the cam 470 is substantially as shown in FIG. 11, the cam 470 will always be in contact with or immediately adjacent these two walls 482, 484 of the cam following orifice 480, restricting movement of the orifice and its associated plate 260'. The distance between the axis 466 of this cam 470 and the adjacent wall 484 is at its minimum, namely radius $R_2$ of that gear. Comparing FIG. 12 to FIG. 13, as the gear 460 is rotated counterclockwise about 90°, this distance between the axis 466 and the wall 484 increases relatively gradually to the larger radius $R_1$ of the cam 470. As the axis 466 of the gear 460 is fixed relative to the base plate 240', this rotation of the gear 460 will urge the first vessel carrying plate 310' toward the left in these drawings, as suggested by the arrow in FIG. 13.

Much like the cam 470 in the cam following orifice 480, each of the cams 420 (shown in phantom) desirably remain engaged with opposed walls of their respective cam following orifices throughout rotation of the gears 410; the cam 420 toward the left of FIG. 12 will engage walls 452 and 454 of the left cam following orifice 450 and the cam 420 toward the right of FIG. 12 will engage walls 442 and 444 of the right cam following orifice 440. The cams 420 do not engage the other walls of the cam following orifices, though, but instead are spaced away from these other walls at all times.

Figure 13:
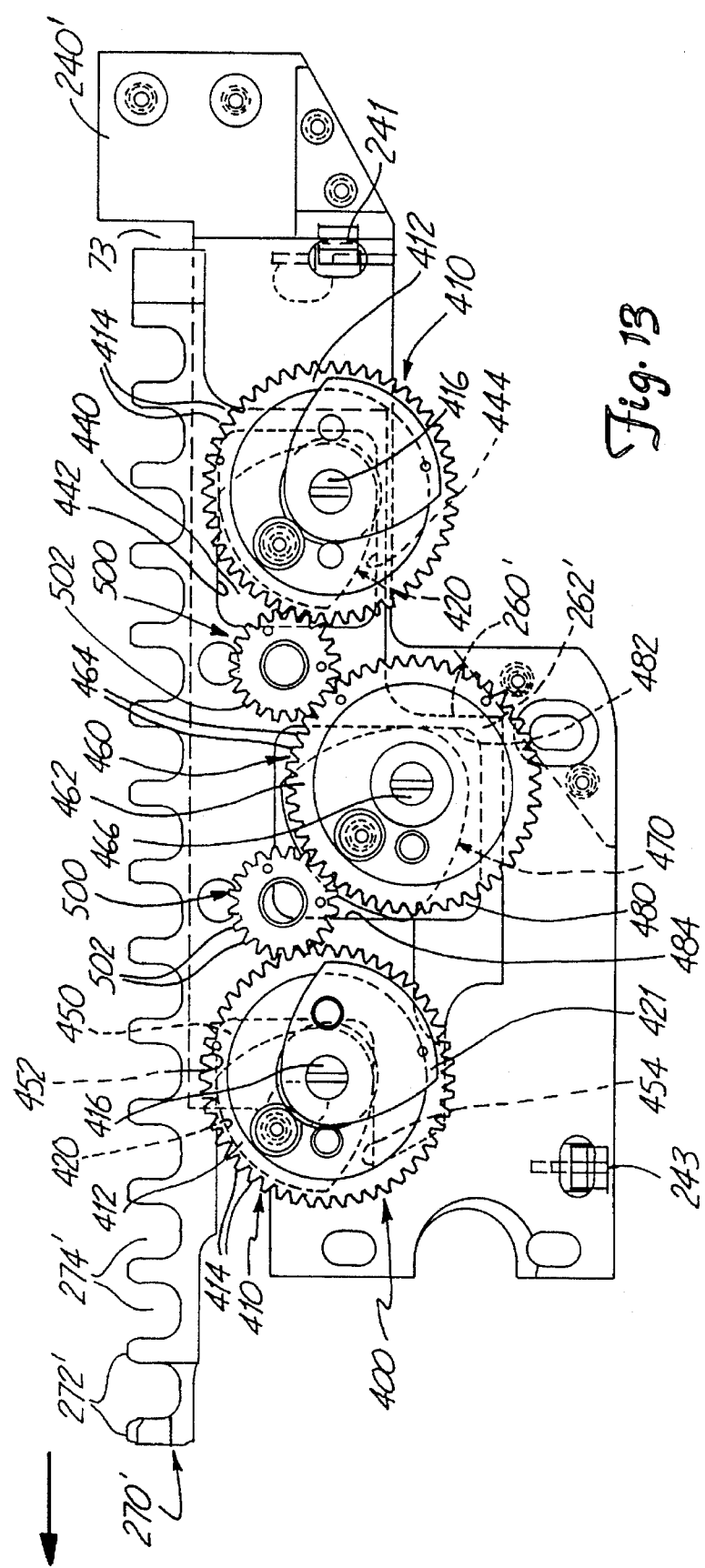

During the 90° or so of rotation of the central actuating gear 460 taking place between FIGS. 12 and 13, the other two actuating gears 410 will also turn about their respective axes. During this rotation, the distance between the axis 416 of the cams 420 and the walls 442, 444 or 452, 454 of their respective orifices 440 or 450 will remain constant. For example, the distance between the axis 416 of the left cam 420 and the forward wall 452 of the left cam following orifice 450 remains approximately equal to the radius $R_1$ of cam 420 and the distance between the axis 416 and the rear wall 454 will remain constant at about radius $R_2$ throughout the rotation of the cam 420 between FIGS. 12 and 13. This will limit the movement of the first vessel carrying plate 260' and ensure that movement of the plate 260' will be substantially confined to the x-axis of FIG. 10. Since the cams 420 do not engage the other walls of their respective cam following orifices during this movement, these cams will not restrict movement of the vessel carrying plate 260' along the x-axis.

Figure 14:
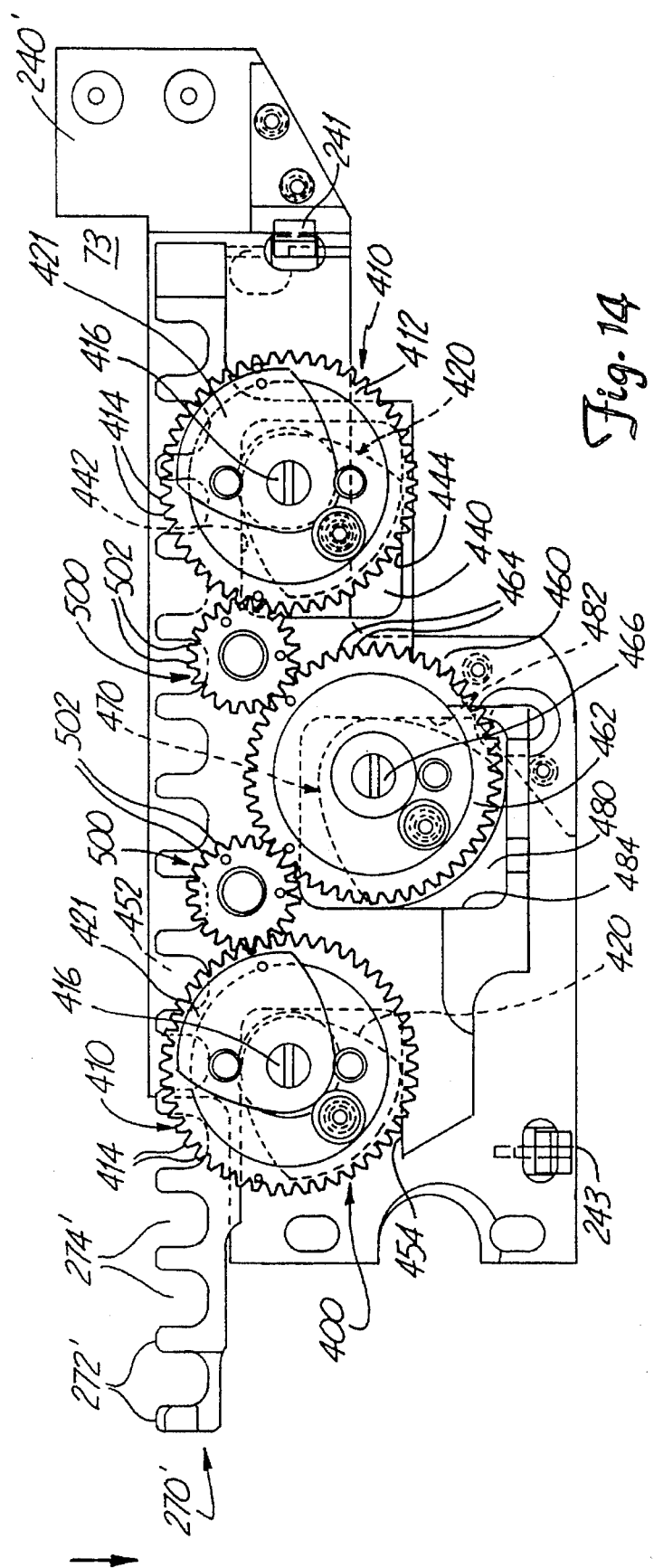

In moving from the positions shown in FIG. 13 to those shown in FIG. 14, the actuating gears 410, 460 are once again rotated about 90°. During this rotation, the distance between the axes 416 of the cams 420 and the abutting walls of the respective cam following orifices will change. For example, in FIG. 13, the distance between the axis 416 of the left cam 420 and the forward wall 452 of the cam following orifice 450 will relatively gradually decrease from about cam radius $R_1$ to about cam radius $R_2$ and the distance between this axis and the rearward wall 454 will simultaneously increase from about radius $R_2$ to about radius $R_1$. Since the axes of the cams 420 are fixed with respect to the base plate 240', this will urge the first vessel carrying plate 260' rearwardly along the x-axis, as illustrated by the arrow in FIG. 14.

Since the distance between the opposed walls 482, 484 of the central cam following orifice is approximately equal to the radius $R_3$ of the cam 470, the cam will always remain in engagement with those walls. Thus, although the distance between the axis 466 of the cam 470 and these walls does not change between FIG. 13 and FIG. 14, the cam 470 will help ensure that movement of the plate 260' will be substantially restricted to the y-axis. The provision of two gears 410 will also help reduce twisting of the plate 260' by urging rearwardly adjacent both ends of the plate. Although this may not be necessary in light of the presence of the cam 470, this will help ensure smooth operation of the vessel shuttle 210' without jamming, which may otherwise occur.

In moving from the position shown in FIG. 14 to that shown in FIG. 15, the actuating gears 410, 460 are once again turned through an angle of about 90°, bringing the total rotation of these gears from FIG. 12 to FIG. 15 to about 270°. During this phase of operation, the distances between the axis 466 of the central cam 470 and the walls 482, 484 of the central cam following orifice 480 change. In particular, the distance between the axis and the fight wall 482 relatively gradually increases frown about cam radius $R_2$ to about cam radius $R_1$ while the distance between the axis and the left wall 484 relatively gradually decreases from about cam radius $R_1$ to about cam radius $R_2$. This, in combination with the presence of cams 420 in cam following orifices 440 and 450, will tend to urge the first vessel carrying plate 260' along the x-axis, as illustrated by the arrow pointing toward the fight in FIG. 15.

Finally, the cam is rotated through another 90° to move between the position depicted in FIG. 15 and the plate's "home" position shown in FIG. 12, bringing the total rotation of the actuating gears 410, 460 to a total of 360°, or one full rotation of the gears. During this rotation, the cams 420 will urge forwardly against the forward walls 442, 452 of their cam following orifices 440 and 450, respectively. This will tend to move the plate 260' forwardly generally along the y-axis into the position shown in FIG. 12, as suggested by the arrow pointing forwardly in that drawing.

As best seen in FIG. 10, the second vessel carrying plate 310' includes two cam following orifices 510, 520. These orifices are also generally rectangular in shape and are adapted to operate in conjunction with the upper cams 421 on the actuating gears 410 to drive the second vessel carrying plate 310' forwardly and rearwardly generally along the y-axis. As with the cams 420 in the cam following orifices 440 and 450, the cams 421 acts against the forward and rearward walls of their respective cam following orifices to drive the vessel carrying plates. In order to ensure that the second vessel carrying plate is driven only in the y-axis, the x-axis dimension of the orifices 510, 520 is wider than their dimension in the y-axis.

In particular, these orifices optimally have a y-axis dimension approximately equal to the radius $R_3$ of the gear 421, or slightly larger to ensure smooth movement of the cam within the orifice. However, the orifices provide sufficient clearance in the x-axis direction to ensure that the cams do not engage the ends of the orifices. As the cams 420 rotate with respect to the first vessel carrying plate 260', the cam following orifices 440, 450 are moved laterally with respect to the cams 420 by operation of the central cam 470. This helps ensure sufficient clearance between the cams 420 and the other walls of their respective orifices. As there is no analogous movement of the second vessel carrying plate in the x-axis, the orifices 510, 520 will tend to have to be wider in the direction of the x-axis than the orifices 440, 450 to maintain enough clearance between the cams and the lateral walls of the second vessel carrying plate.

The dimensions of the cams 421 are substantially the same as those of the cams 420 and the depths of the cam following orifices 510, 520 of the second vessel carrying plate 310' are substantially the same as the depth of the cam following orifices 440, 450 of the first vessel carrying plate 260', with the depths of all four of these orifices being approximately equal to the radius $R_3$ of the cams 420 and 421, as noted above. Hence, the operation of the cams 421 in their respective orifices and the net motion of the plate 310' is substantially the same as the interaction between cams 420 and their respective orifices and the net motion of the plate 260' caused by the cams 420.

However, the cams 421 are directly out of phase with the cams 420 on the other side of the actuating gears 410, i.e. the cams 421 are oriented about 180° away from the orientation of the cams 420 about their shared axis. Thus, while the cams 420 are idling in their respective orifices 440, 450 in the first vessel carrying plate (e.g. between FIG. 12 and FIG. 13), the cams 421 will also idle in their orifices 510, 520 and will induce no net movement of the plate 310'. However, when the cams 420 do cause the first vessel carrying plate 260' to move in one direction along the y-axis, i.e. either forwardly or rearwardly, the cams 421 will cause the second vessel carrying plate 310' to move in the other direction along the y-axis.

The operation of the first embodiment of a vessel shuttle 210 of the invention was explained in connection with FIGS. 4–7. The vessel shuttle 210' of the present embodiment operates in much the same fashion, including the general operation of advancing or retracting a vessel along a path on the floor 73. The primary significant difference in operation, though, is in the overlap of certain motions in the present embodiment.

In the embodiment of FIG. 2, the first and second vessel carrying beams 260 and 310, respectively, are moved along the y-axis in separate movements, i.e. one of the plates is moved forwardly to engage the vessels 52 before retraction of the other plate begins. In the present embodiment, cams 420 and 421 act against their respective plates 260' and 310' at the same time, such that as one of the plates is moved forwardly the other is simultaneously being retracted. Nonetheless, the vessels are always supported by at least one set of fingers 272' or 322' at any given time. In all other relevant respects, the vessel shuttle 210' of this embodiment operates substantially as described in connection with FIGS. 4–7 for the first embodiment of the vessel shuttle 210.

The vessel shuttles 210 and 210' of the invention each provide a relatively compact system for moving reaction vessels through chemical analyzers and the like. These vessel shuttles move the vessels along an essentially linear path on the floor 73. Since the vessel shuttles themselves are relatively small and they move the vessels along a straight path rather than a more complex, space-consuming path, valuable space in an analyzer can be conserved, helping make the analyzer itself more compact. Also, by moving the vessel carrying plates relatively smoothly between their different positions as described above, the vessels are not subjected to sudden acceleration or deceleration. This relatively smooth movement of the vessels will tend to reduce splashing of the vessels' contents, improving the reliability of the results of any tests performed on the samples.

Although either of the vessel shuttles 210 or 210' of the invention achieve these ends, the second embodiment of the invention is generally preferred. As noted above, the design of this vessel shuttle 210' has fewer parts than the vessel shuttle 210. It is believed that this reduction in the number of pans will result in greater operational reliability and reduced manufacturing and maintenance costs. Further savings in manufacturing costs may also be realized if the gears 410, 460 of the shuttle 210' are integrally molded with their associated cams (i.e. cams 420 and 421 for gear 410 and cam 470 for gear 460), such as from a durable, wear resistant polymeric material such as Delrin. Although the pans of the vessel shuttle 210 could also be made from such materials, it is believed that the second vessel shuttle 210' may be more readily formed of such materials yet still achieve the necessary tolerances and durability than would the first vessel shuttle 210.

In one further preferred embodiment of the invention, a waste chute 162 is positioned adjacent the path 58 of the incubator at a position opposite the vessel shuttle 210 or 210'. This waste chute 162 can be readily employed with either embodiment of the vessel shuttle of the invention, but neither embodiment of the vessel shuttle includes a finger which extends on the opposite side of the incubation path when the incubator belt is moving. Unless some structure is provided opposite the vessel shuttle, vessels may fall out of the incubator during normal operation and fall onto the waste chute 162.

Figure 8:
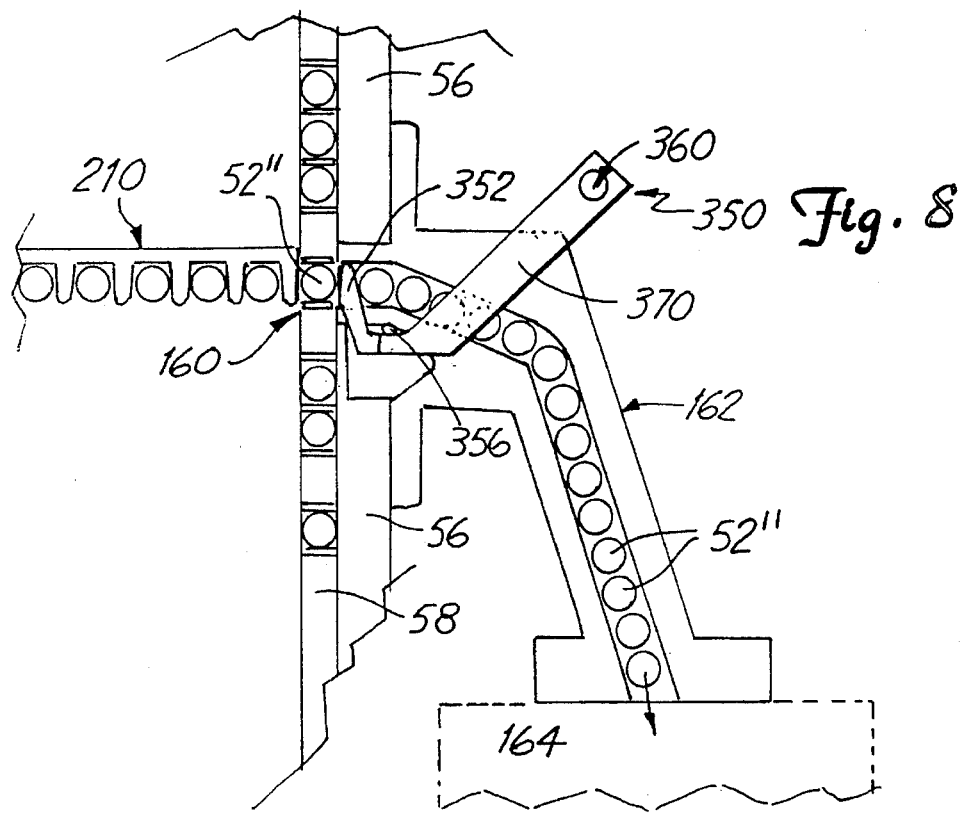
FIG. 8 is a top view of a waste path door means for use in the analyzer of FIG. 1.
Figure 9:
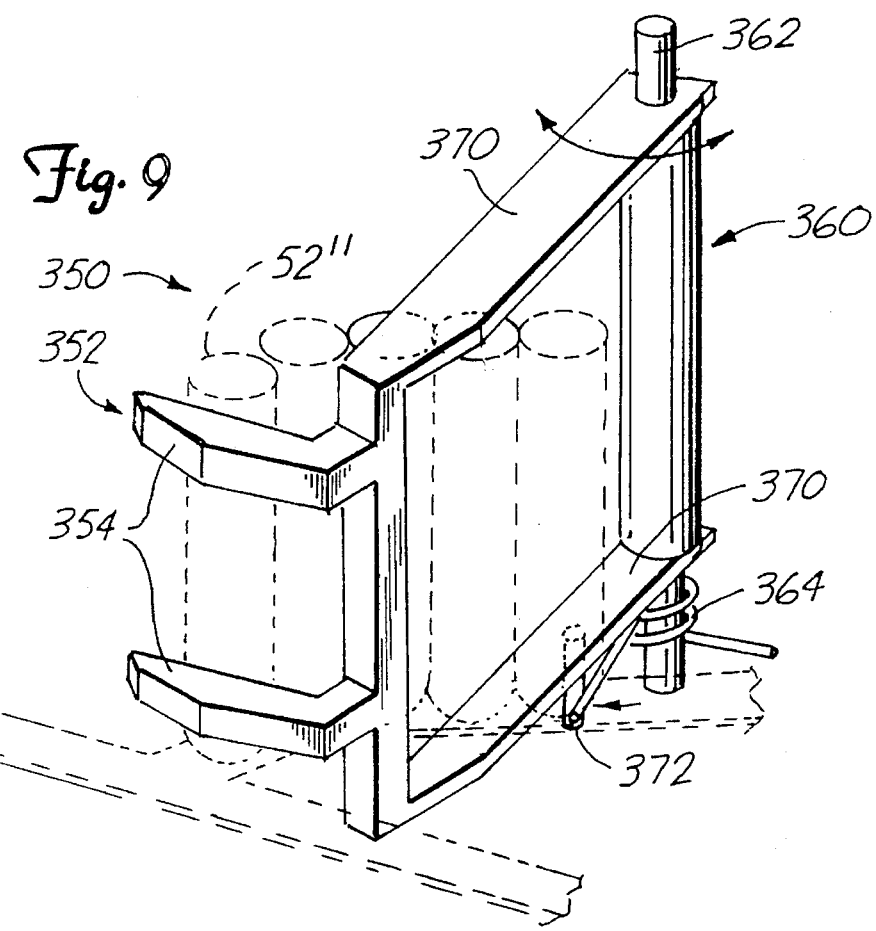
FIG. 9 is a perspective isolation view of the waste path door means of FIG. 8.

Hence, the vessel transport of this embodiment may also include a waste chute gate 350, shown in FIGS. 1, 8 and 9. The waste chute gate 350 described herein may be adapted for use as a gate mechanism anywhere in an analyzer. The waste chute gate includes a door 352 attached to a hinge means 360 by an elongate actuating arm 370. As best seen in FIGS. 1 and 8, when the door 352 is in its normal position, it is positioned adjacent the incubation path. The opening of the waste chute 162 defines a gap in the wall 56 of the incubator and the door 352 is normally biased into position to bridge this gap, presenting a fairly solid wall which prevents the vessels 52 on the incubator from falling off the incubator.

When a spent vessel 52" is to be ejected from the incubator onto the waste chute 162 for disposal, it is positioned at the incubator transfer station 160. This transfer station 160 is immediately adjacent the vessel shuttle 210 at the end of the path of the vessel shuttle and along the path of the incubator immediately adjacent the waste chute. When the first vessel carrying beam 270 is moved into the incubation path to load a new vessel, the outermost finger 272 of that beam, which defines a leading edge of the beam, passes through the incubator transfer station 160. In so doing, the first vessel carrying beam passes beneath the fingers 68 of the carrier 64 as shown in FIGS. 5 and 6, avoiding any contact between the vessel carrying beam and the carriers of the incubator belt. When the first beam 270 is so moved, the finger will abut against any vessel in the incubator transfer station 160 and urge it against the door 352 of the waste chute gate.

As shown in FIG. 9, the waste chute gate 350 pivots about a hinge 360 which includes a pivot pin 362 and a biasing spring 364. The biasing spring 364 acts against a stop pin 372 on the arm 370 of the gate, urging the gate toward its closed position wherein it abuts the gate stop 356 (illustrated in FIGS. 1 and 8). When the first vessel carrying beam 270 urges a vessel in the incubator transfer station 160 against the door 252, this vessel will cause the door to open because the force applied by the vessel is spaced radially outwardly from the hinge means 360. When the gate 250 pivots in response to the urging of the spent vessel (counterclockwise in FIG. 8), the door will pivot out of the position shown in FIGS. 1 and 8, permitting the vessel to pass onto the waste chute.

It should be noted that this causes the door to move in a direction generally parallel to the path of the incubator rather than swinging inwardly into the waste chute. If the door had to swing inwardly into the waste chute, such as if the door were pivoted about a point immediately adjacent the incubator transfer station 160 at the entrance of the waste chute, the spent vessel would have to move along the waste chute far enough to permit clearance for the door to swing shut again. By having the door move generally parallel to the incubation path, i.e. generally perpendicular to the waste chute, the vessel need only clear the thickness of the door before the door is allowed to pivot back into its normal, closed position.

The movement of the door 352 in accordance with this embodiment of the invention permits a single spent vessel 52" to open the door sufficiently to pass into the waste chute. If the vessel had to move too far down the chute to provide clearance for the door, the spent vessel may not move down the chute far enough to permit the door to close, hindering operation of the incubator 50.

The newly added spent vessel will then urge the row of vessels along the waste chute 162, ejecting the last vessel into the waste container 164 for disposal. In a preferred embodiment, the waste chute includes a restraining means, such as resilient tabs or the like (not shown), at the end adjacent the waste container so that vessels will remain along the waste chute until forced into the waste container. This will allow the vessels to support one another along the waste chute, preventing the vessels from inadvertently falling over and spilling their contents in the analyzer. Once the spent vessel is added to the waste chute 162, the waste chute gate will close again (returning to the position depicted in FIGS. 1 and 8) in response to the biasing force of the spring 364 of the hinge means.

If the waste container 164 becomes full, vessels will be backed up along the waste chute. If the waste chute gate 350 were not in place, the vessels could be urged back along the waste chute and dislodge vessels on the incubator. The presence of the waste chute gate prevents this from happening, though. Furthermore, when vessels do become backed up and they tend to urge one another back along the waste chute, the first vessel in the chute will be urged against the rear of the door 352 of the gate. As this force is in the opposite direction of the force exerted by a new vessel being added to the chute by operation of the vessel shuttle 210, the force of the extra vessels along the chute will actually help force the waste chute door closed, helping to isolate the spent vessels from those along the incubator.

If so desired, the door 352 may be a substantially solid plate or the like. However, it is preferred that a pair of flanges 354 be used instead. When the first vessel carrying beam 270 moves into position to place a new vessel on the incubator, the beam will extend beyond the incubation path. The leading edge of the beam 270 will therefore extend into the position occupied by the door 352. If the door were in the way of the beam, the beam itself would tend to abut against the door and cause it to open; this is not desired because the door should only open when it is necessary to add a new vessel to the waste chute. If the door were to open any time the beam 270 moved into the position show in FIGS. 5 and 6, the door would open when a vessel is being retracted from the incubator belt for addition of second stage reagents, possibly permitting a spent vessel to either be inadvertently added to the incubator or fall over, spilling its contents in the incubator.

In a preferred embodiment, the door is configured to permit the first vessel carrying beam 270 to move freely without directly contacting the door. In the embodiment shown in FIG. 9, the flanges 354 of the door are both above the height of the top of the first vessel carrying beam 270. This permits the beam 270 to simply pass beneath the door and the door will open only if a vessel is present at the incubation transfer station 160 and is urged toward the waste chute 162 by the beam 270. If so desired, the door may instead be configured with flanges spaced apart sufficiently to permit the vessel carrying beam 270 to pass therebetween, avoiding direct contact between the door and the beam.

The motor rotating the drive shaft of the vessel shuttle 210 is not adapted to operate while the incubator belt is being moved; if the vessel shuttle were to move while the incubator belt is moving, the first vessel carrying plate 260 could extend into the path of the incubator and interrupt movement of the incubator belt. The vessel shuttle's driver, which may include the motor and the drive shaft 220, is restricted to movement when the incubator belt is still. It should also noted that the vessel shuttle is not adapted to move when the pipettor of the assay constituents delivery means is within a vessel at the access location of the delivery means on the path of the vessel shuttle. If the vessel shuttle were permitted to advance vessels while the probe was inserted in a vessel along the vessel shuttle path, the probe would interfere in operation of the shuttle.

While a preferred embodiment of the present invention has been described, it should be understood that various changes, adaptations and modifications may be made therein without departing from the spirit of the invention and the scope of the appended claims.

What is claimed is:

1. An apparatus for moving reaction vessels to or from an assay resource station in an automated chemical analyzer comprising a vessel shuttle having a plurality of movable plates and at least two cams, the plates including first and second vessel carrying plates adapted to move cooperatively with respect to one another to advance one of said vessels stepwise along a generally linear path without net motion of the first and second vessel carrying plates as the vessel is advanced one step, the first and second vessel carrying plates each comprising a plurality of fingers defining recesses for receiving vessels, the first vessel carrying plate having at least one cam following orifice and the second vessel carrying plate having at least two cam following orifices, said cam following orifices receiving and coacting with said cams to move the first vessel carrying plate in a direction substantially perpendicular to said linear path and to move the second vessel carrying plate rectilinearly both generally parallel to and generally perpendicular to said linear path, one of the first and second vessel carrying plates being disposed generally vertically above the other of the first and second vessel carrying plates.

2. The apparatus of claim 1 wherein each of said cams have an axis and four arcuate sides, a first of said sides defining an arc having a substantially constant radius $R_1$ about said axis, a second of said sides defining an arc having a substantially constant radius $R_2$ about said axis, $R_1$ being greater than $R_2$, a third of said sides extending between first ends of each of said first and second sides and defining an arc having a substantially constant radius $R_3$ about a second end of the first side, and a fourth of said sides extending between second ends of each of said first and second sides and defining an arc having the same radius $R_3$ about the first end of the first side.

3. The apparatus of claim 2 wherein the cam following orifices are generally rectangular in shape.

4. The apparatus of claim 3 wherein at least one of said cam following orifices has a first pair of opposed walls spaced from one another a distance approximately equal to said radius $R_3$ of the cam received therein and a second pair of opposed walls spaced from one another a distance greater than said radius $R_3$ to substantially avoid abutting contact with said cam as the cam is rotated within the orifice.

5. The apparatus of claim 1 wherein the each of the first and second vessel carrying plates is adapted to move from a forward position wherein a vessel is supportingly received in a recess to a rearward position wherein no vessel is received in the recess, at least one of the vessel carrying plates being adapted to be in its forward position when the other of the vessel carrying plates is in its rearward position.

6. The apparatus of claim 1 wherein the first vessel carrying plate is adapted to move laterally with respect to the second vessel carrying plate.

7. The apparatus of claim 1 wherein each of the first and second vessel carrying plates has a body from which one of said pluralities of fingers extends outwardly, the body of each vessel carrying plate being disposed on the same side of said generally linear path.

8. The apparatus of claim 7 wherein the body and the fingers of each vessel carrying plate are together adapted to support three sides of a vessel received therein, the apparatus further comprising a row of vessels disposed along a side of said linear path disposed opposite the bodies of the vessel carrying plates.

* * * * *